US012611164B2

(12) United States Patent
Ebata

(10) Patent No.: US 12,611,164 B2
(45) Date of Patent: Apr. 28, 2026

(54) ULTRASOUND DIAGNOSTIC APPARATUS WITH FUNCTION FOR HIGHLIGHT-DISPLAYING EXCREMENT REGION IN ULTRASOUND IMAGE AND CONTROL METHOD FOR ULTRASOUND DIAGNOSTIC APPARATUS

(71) Applicant: FUJIFILM Corporation, Tokyo (JP)

(72) Inventor: Tetsurou Ebata, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 110 days.

(21) Appl. No.: 18/540,789

(22) Filed: Dec. 14, 2023

(65) Prior Publication Data

US 2024/0108308 A1 Apr. 4, 2024

Related U.S. Application Data

(63) Continuation of application No. PCT/JP2022/018997, filed on Apr. 27, 2022.

(30) Foreign Application Priority Data

Jun. 24, 2021 (JP) ................................. 2021-105100

(51) Int. Cl.
*A61B 8/08* (2006.01)
*A61B 8/00* (2006.01)
(52) U.S. Cl.
CPC .......... *A61B 8/0833* (2013.01); *A61B 8/4461* (2013.01); *A61B 8/461* (2013.01); *A61B 8/5207* (2013.01); *A61B 8/5284* (2013.01)
(58) Field of Classification Search
CPC ........ A61B 8/461; A61B 8/469; A61B 8/4254
See application file for complete search history.

(56) References Cited

U.S. PATENT DOCUMENTS

2003/0105401 A1* 6/2003 Jago ....................... A61B 8/467
600/443
2009/0149752 A1* 6/2009 Osaka .................... A61B 8/463
600/443

(Continued)

FOREIGN PATENT DOCUMENTS

JP 2008-161674 A 7/2008
JP 2012-120747 A 6/2012

(Continued)

OTHER PUBLICATIONS

JP-2016195748-A (Year: 2016).*

(Continued)

*Primary Examiner* — Nyrobi Celestine
(74) *Attorney, Agent, or Firm* — Studebaker Brackett PLLC

(57) ABSTRACT

To highlight-display an excrement region in an ultrasound image so as not to interfere with the user's interpretation of the ultrasound image. In an ultrasound diagnostic apparatus and a control method for the ultrasound diagnostic apparatus according to the present invention, an excrement information detection unit performs detection processing for detecting an excrement region from an ultrasound image. A highlight level determination unit determines a highlight level of the excrement region based on a determination condition for determining the highlight level of the excrement region in a case where the excrement region is detected. An excrement information display unit highlight-displays the excrement region in the ultrasound image displayed on a monitor according to the highlight level determined by the highlight level determination unit.

28 Claims, 12 Drawing Sheets

(56)                References Cited

U.S. PATENT DOCUMENTS

| | | | | |
|---|---|---|---|---|
| 2012/0087564 | A1* | 4/2012 | Tsujita | A61B 8/5223 |
| | | | | 382/131 |
| 2014/0031687 | A1* | 1/2014 | Kurita | A61B 8/54 |
| | | | | 600/440 |
| 2014/0193099 | A1* | 7/2014 | Yoshikawa | G06T 7/337 |
| | | | | 382/295 |
| 2015/0164476 | A1* | 6/2015 | Kong | G01S 7/52022 |
| | | | | 600/438 |
| 2015/0182198 | A1* | 7/2015 | Sabourin | A61B 8/469 |
| | | | | 600/440 |
| 2017/0086791 | A1* | 3/2017 | Chae | A61B 8/13 |
| 2017/0301088 | A1* | 10/2017 | Bharat | A61B 34/20 |
| 2018/0064413 | A1* | 3/2018 | Nakanishi | A61B 8/4427 |
| 2018/0132828 | A1* | 5/2018 | Park | A61B 8/463 |
| 2019/0209131 | A1* | 7/2019 | Ebata | A61B 8/4254 |
| 2019/0216441 | A1* | 7/2019 | Matsumoto | A61B 8/0833 |
| 2020/0129160 | A1 | 4/2020 | Ebata | |
| 2020/0222030 | A1* | 7/2020 | Park | A61B 8/4254 |
| 2021/0219960 | A1* | 7/2021 | Tsutaoka | A61B 8/467 |

FOREIGN PATENT DOCUMENTS

| | | | | |
|---|---|---|---|---|
| JP | 2016195748 | A | * | 11/2016 |
| JP | 6745796 | B2 | | 8/2020 |
| JP | 2021-84000 | A | | 6/2021 |
| WO | 2020/075449 | A1 | | 4/2020 |

OTHER PUBLICATIONS

International Search Report issued in PCT/JP2022/018997; mailed Jun. 21, 2022.

International Preliminary Report on Patentability (Chapter I) and Written Opinion of the International Searching Authority issued in PCT/JP2022/018997; issued Dec. 14, 2023.

Extended European Search Report issued in EP 22 82 8072.3-1122 by the European Patent Office on Oct. 30, 2024 which is related to U.S. Appl. No. 18/540,789.

"Notice of Reasons for Refusal" Office Action issued in JP 2023-529664; mailed by the Japanese Patent Office on Jul. 22, 2025.

* cited by examiner

FIG. 9

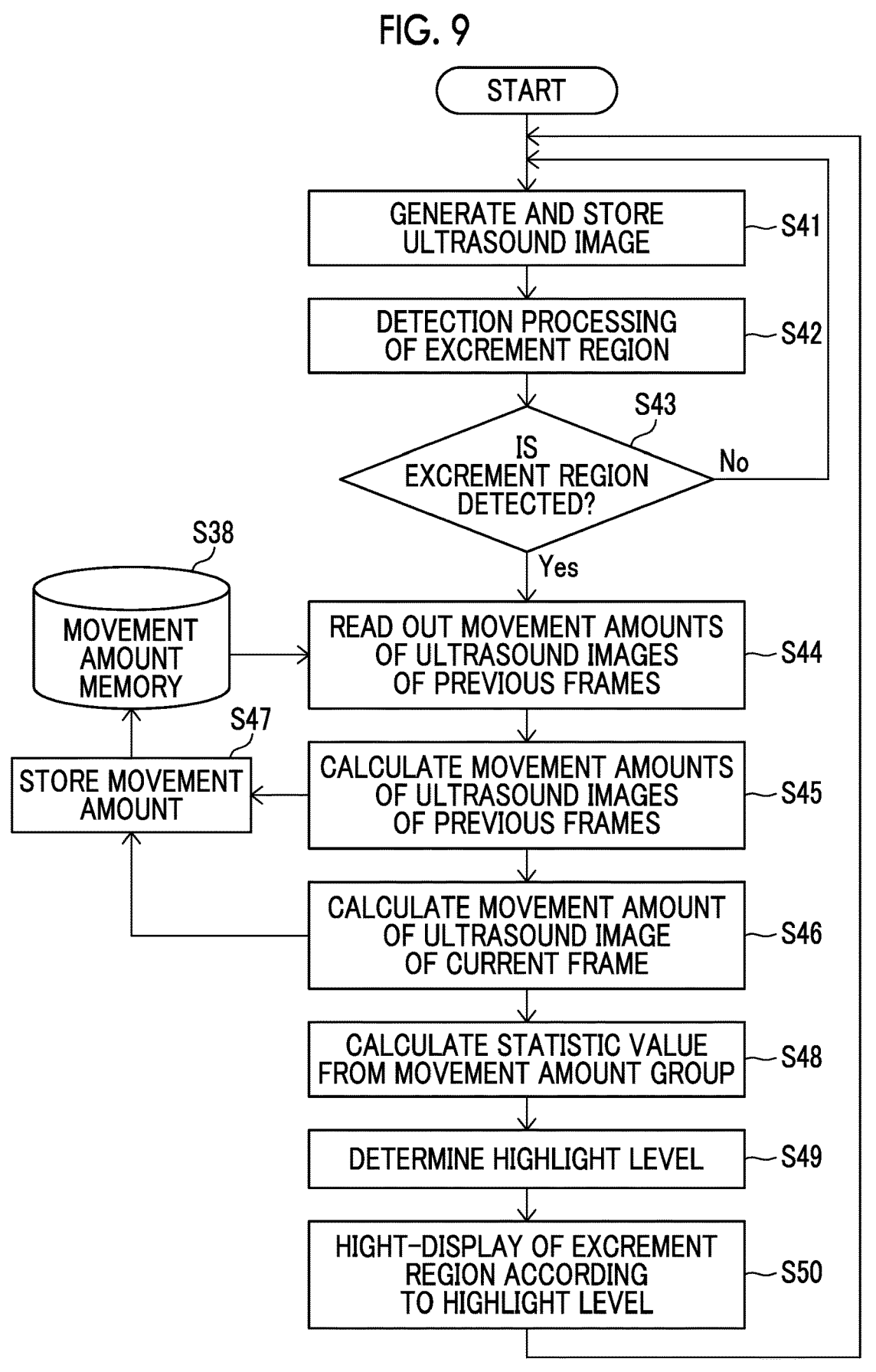

START

GENERATE AND STORE
ULTRASOUND IMAGE — S41

DETECTION PROCESSING
OF EXCREMENT REGION — S42

IS
EXCREMENT REGION
DETECTED? — S43      No

Yes

MOVEMENT
AMOUNT
MEMORY — S38

READ OUT MOVEMENT AMOUNTS
OF ULTRASOUND IMAGES
OF PREVIOUS FRAMES — S44

STORE MOVEMENT
AMOUNT — S47

CALCULATE MOVEMENT AMOUNTS
OF ULTRASOUND IMAGES
OF PREVIOUS FRAMES — S45

CALCULATE MOVEMENT AMOUNT
OF ULTRASOUND IMAGE
OF CURRENT FRAME — S46

CALCULATE STATISTIC VALUE
FROM MOVEMENT AMOUNT GROUP — S48

DETERMINE HIGHLIGHT LEVEL — S49

HIGHT-DISPLAY OF EXCREMENT
REGION ACCORDING
TO HIGHLIGHT LEVEL — S50

47

47

48

48

PRESENCE OF HARD EXCREMENT

ULTRASOUND DIAGNOSTIC APPARATUS WITH FUNCTION FOR HIGHLIGHT-DISPLAYING EXCREMENT REGION IN ULTRASOUND IMAGE AND CONTROL METHOD FOR ULTRASOUND DIAGNOSTIC APPARATUS

CROSS-REFERENCE TO RELATED APPLICATIONS

This application is a Continuation of PCT International Application No. PCT/JP2022/018997 filed on Apr. 27, 2022, which claims priority under 35 U.S.C. § 119(a) to Japanese Patent Application No. 2021-105100 filed on Jun. 24, 2021. The above applications are hereby expressly incorporated by reference, in their entirety, into the present application.

BACKGROUND OF THE INVENTION

1. Field of the Invention

The present invention relates to an ultrasound diagnostic apparatus having a function of detecting an excrement region in an ultrasound image and highlight-displaying the excrement region in the ultrasound image displayed on a monitor and a control method for the ultrasound diagnostic apparatus.

2. Description of the Related Art

In recent years, a technique of performing constipation diagnosis including evaluation of the presence or absence of excrement and evaluation of excrement properties such as hard excrement, soft excrement, and normal excrement by using an ultrasound image has been proposed.

For example, WO2020/075449A discloses an ultrasound diagnostic apparatus that performs constipation evaluation such as whether excrement existing in a rectum of a subject is soft excrement or hard excrement by performing image analysis on an ultrasound image and displays a constipation evaluation result on a display unit.

In addition, although the content is not related to constipation, JP6745796B discloses an intervention treatment system that displays an outer edge contour of a target of interest such as a prostate in an image slice of a standard image data set corresponding to a current ultrasound image by superimposing the outer edge contour on the current ultrasound image.

On the other hand, the constipation diagnosis using an ultrasound image has not yet become fully widespread as a diagnosis method and an examination method. As a result, even a skilled person has difficulty in interpreting excrement in the ultrasound image. In addition, it is very difficult for an inexperienced person or an unskilled person to interpret the ultrasound image itself.

SUMMARY OF THE INVENTION

By detecting an excrement region by analyzing an ultrasound image and highlight-displaying the excrement region in the ultrasound image displayed on a monitor, in constipation diagnosis using ultrasound images, it can be expected that the highlight display will help an inexperienced person and an unskilled person to diagnose constipation.

However, in a case where an excrement region of the ultrasound image displayed on the monitor is continuously highlight-displayed when scanning an examination area of a subject by a user (examiner) in real time, the highlight display may interfere with the user's interpretation of the ultrasound image. In particular, in constipation diagnosis, since the user determines the presence or absence of excrement and an excrement property based on a brightness difference between the excrement region and a region around the excrement region, in a case where the excrement region is continuously highlight-displayed, the user cannot check the presence or absence of excrement and an excrement property.

Therefore, an object of the present invention is to provide an ultrasound diagnostic apparatus and a control method for an ultrasound diagnostic apparatus capable of highlight-displaying an excrement region in an ultrasound image so as not to interfere with user's interpretation of the ultrasound image.

In order to achieve the above object, according to an aspect of the present invention, there is provided an ultrasound diagnostic apparatus including: an ultrasound probe; a monitor; an image generation unit that generates an ultrasound image based on a reception signal obtained by scanning an examination area of a subject with ultrasound beams using the ultrasound probe; a display control unit that displays the ultrasound image on the monitor; an excrement information detection unit that performs detection processing for detecting an excrement region from the ultrasound image; a highlight level determination unit that determines a highlight level of the excrement region based on a determination condition for determining the highlight level of the excrement region in a case where the excrement region is detected; and an excrement information display unit that highlight-displays the excrement region in the ultrasound image displayed on the monitor according to the highlight level determined by the highlight level determination unit.

Here, preferably, the excrement information detection unit detects the excrement region from the ultrasound image by using at least one of template matching, machine learning using image feature amounts, or a deep learning model.

Further, preferably, the ultrasound diagnostic apparatus further includes a movement amount detection unit that detects a movement amount of the ultrasound probe, in which the highlight level determination unit determines the highlight level based on the movement amount.

Further, preferably, the movement amount detection unit obtains, for each frame of the ultrasound images, a correlation value between an ultrasound image of a current frame and an ultrasound image of a previous frame that is previous to the current frame by one frame, as the movement amount.

Further, preferably, the movement amount detection unit obtains, for each frame of the ultrasound images, a correlation value between an ultrasound image of a current frame and an ultrasound image of a previous frame that is previous to the ultrasound image of the current frame by a predetermined number of frames, as the movement amount.

Further, preferably, the movement amount detection unit obtains, for each frame of the ultrasound images, a degree of superimposition between the excrement region of an ultrasound image of a current frame and the excrement region of an ultrasound image of a previous frame that is previous to the current frame by one frame, as the movement amount.

Further, preferably, the movement amount detection unit obtains, for each frame of the ultrasound images, a movement amount between an ultrasound image of a current frame and an ultrasound image of a previous frame that is previous to the current frame by one frame, as a movement amount of the ultrasound image of the current frame, and obtains a statistic value obtained from a movement amount group consisting of the movement amount of the ultrasound image of the current frame and movement amounts of ultrasound images of a predetermined number of previous frames, as the movement amount.

Further, preferably, the statistic value is an average value obtained from the movement amount group, a weighted average value obtained from the movement amount group by using a weight increasing from a past to a present, or a median value obtained from the movement amount group.

Further, preferably, the ultrasound diagnostic apparatus further includes a movement amount memory that stores the movement amount, in which the excrement information detection unit performs the detection processing of the excrement region for each frame of the ultrasound images, and the movement amount detection unit obtains the movement amount for each frame of the ultrasound images, and stores the movement amount in the movement amount memory, and in a case where the excrement region is detected, reads out the movement amounts of the ultrasound images of the predetermined number of previous frames from the movement amount memory, and obtains the statistic value from the movement amount group consisting of the movement amount of the ultrasound image of the current frame and the movement amounts of the ultrasound images of the previous frames that are read out from the movement amount memory.

Further, preferably, the ultrasound diagnostic apparatus further includes a movement amount memory that stores the movement amount, in which the excrement information detection unit performs the detection processing of the excrement region for each frame of the ultrasound images, and in a case where the excrement region is detected, the movement amount detection unit reads out, from the movement amount memory, the movement amount of the ultrasound image of the previous frame that is stored in the movement amount memory, as a first movement amount, in a case where the movement amount of the ultrasound image of the previous frame that is stored in the movement amount memory is included in the movement amounts of the ultrasound images of the predetermined number of previous frames, obtains the movement amount of the ultrasound image of the previous frame that is not stored in the movement amount memory, as a second movement amount, in a case where the movement amount of the ultrasound image of the previous frame that is not stored in the movement amount memory is included in the movement amounts of the ultrasound images of the predetermined number of previous frames, obtains the movement amount of the ultrasound image of the current frame, as a third movement amount, stores the second movement amount and the third movement amount in the movement amount memory, and obtains the statistic value from a movement amount group consisting of the first movement amount, the second movement amount, and the third movement amount.

Further, preferably, the movement amount detection unit detects the movement amount based on a movement detection result by a motion sensor provided in the ultrasound probe.

Further, preferably, the movement amount detection unit performs two-value determination for determining movement of the ultrasound probe with two-values indicating presence of movement or absence of movement, based on the movement amount, and the highlight level determination unit determines a first highlight level in a case where presence of the movement is determined, and determines a second highlight level lower than the first highlight level in a case where absence of the movement is determined, the first highlight level and the second highlight level being two-stage highlight levels corresponding to the movement of the ultrasound probe with two-values.

Further, preferably, the movement amount detection unit performs multi-value determination for detecting movement of the ultrasound probe with multi-values of three or more values, based on the movement amount, and the highlight level determination unit determines, as the highlight level, a highlight level of a stage corresponding to a determination result of the multi-value determination, from among multi-stage highlight levels corresponding to the movement of the ultrasound probe with multi-values.

Further, preferably, in a case where the determination result of the multi-value determination is changed, the highlight level determination unit changes the highlight level in an ultrasound image of a frame immediately after the determination result of the multi-value determination is changed, to a highlight level of a stage corresponding to the determination result of the multi-value determination after the change.

Further, preferably, in a case where the determination result of the multi-value determination is changed by two or more values, the highlight level determination unit gradually changes the highlight level in ultrasound images of a plurality of frames after the determination result of the multi-value determination is changed, from a highlight level of a stage corresponding to the determination result of the multi-value determination before the change to a highlight level of a stage corresponding to the determination result of the multi-value determination after the change.

Further, preferably, the highlight level determination unit performs identity determination to determine whether or not the excrement regions in ultrasound images of adjacent frames are the identical excrement region, and determines the highlight level based on a continuous display time of the excrement region determined to be the same.

Further, preferably, the highlight level determination unit determines the highlight level based on an area of the excrement region.

Further, preferably, the excrement information display unit creates a mask obtained by coloring and filling an inside of the excrement region with a predetermined display color, changes transparency of the display color according to the highlight level, and displays the mask of which the transparency is changed by superimposing the mask on the excrement region.

Further, preferably, the excrement information display unit creates a contour line by detecting a contour of the excrement region, changes a thickness of the contour line or transparency of a display color of the contour line according to the highlight level, and displays the contour line of which the thickness or the transparency is changed by superimposing the contour line on the contour of the excrement region.

Further, preferably, in a case where the highlight level is equal to or higher than a threshold value, the excrement information display unit creates a mask obtained by coloring and filling an inside of the excrement region with a predetermined display color, and displays the mask by superimposing the mask on the excrement region, and in a case where the highlight level is lower than the threshold value, the excrement information display unit creates a contour line by detecting a contour of the excrement region, and displays the contour line by superimposing the contour line on the contour of the excrement region.

Further, preferably, the excrement information display unit highlight-displays the excrement region by thinning out a frame for the highlight-display according to the highlight level.

Preferably, the excrement information detection unit further performs detection processing for detecting an excrement property of the excrement region from the ultrasound image, and the excrement information display unit changes a display color of the highlight-display of the excrement region according to the excrement property in a case where the excrement property is detected.

Further, preferably, the excrement information detection unit detects a statistic value of brightness in the excrement region for each frame of the ultrasound images, obtains a first comparison result by comparing the statistic value of brightness in the excrement region with a threshold value, and detects the excrement property based on the first comparison result in ultrasound images of one frame or a plurality of frames, or the excrement information detection unit detects a brightness ratio between the statistic value of the brightness in the excrement region and a statistic value of brightness in a predetermined region around the excrement region for each frame of the ultrasound images, obtains a second comparison result by comparing the brightness ratio with a threshold value, and detects the excrement property based on the second comparison result in ultrasound images of one frame or a plurality of frames.

Further, preferably, the excrement information detection unit detects the excrement region by using a deep learning model.

Further, preferably, the highlight level determination unit performs identity determination to determine whether or not the excrement regions of ultrasound images of adjacent frames are the identical excrement region, and temporarily increases the highlight level in a case where a detection result of the excrement property of the excrement region determined to be the same is changed.

Further, preferably, the excrement information display unit displays a detection result of the excrement property on the monitor as text information.

Further, preferably, the highlight level determination unit changes the highlight level according to an instruction from a user.

Further, preferably, the ultrasound diagnostic apparatus has at least two operation modes among a first operation mode in which the excrement region is not highlight-displayed, a second operation mode in which the excrement region is highlight-displayed at a predetermined highlight level regardless of the determination condition, and a third operation mode in which the highlight level is determined based on the determination condition and the excrement region is highlight-displayed, and the ultrasound diagnostic apparatus further includes a mode switching unit that switches an operation mode to one operation mode among the at least two operation modes according to an instruction from a user.

Further, according to another aspect of the present invention, there is provided a control method for an ultrasound diagnostic apparatus, the method including: a step of generating, via an image generation unit, an ultrasound image based on a reception signal obtained by scanning an examination area of a subject with ultrasound beams using an ultrasound probe; a step of displaying, via a display control unit, the ultrasound image on a monitor; a step of performing, via an excrement information detection unit, detection processing for detecting an excrement region from the ultrasound image; a step of determining, via a highlight level determination unit, a highlight level of the excrement region based on a determination condition for determining the highlight level of the excrement region in a case where the excrement region is detected; and a step of highlight-displaying, via an excrement information display unit, the excrement region in the ultrasound image displayed on the monitor according to the highlight level determined in the step of determining the highlight level of the excrement region.

In the aspects of the present invention, the excrement region is highlight-displayed in the ultrasound image displayed on the monitor according to the highlight level determined based on the determination condition of the highlight level. Therefore, the user can easily recognize the excrement region in the ultrasound image in a case where the highlight level is determined to be higher according to the determination condition, and the user can perform interpretation of the ultrasound image without interference by the highlight-display in a case where the highlight level is determined to be lower.

BRIEF DESCRIPTION OF THE DRAWINGS

FIG. 9 is a flowchart of another embodiment illustrating an operation of the ultrasound diagnostic apparatus in a case of obtaining a statistic value from a group of movement amounts of ultrasound images of a plurality of frames.

DESCRIPTION OF THE PREFERRED EMBODIMENTS

Hereinafter, an ultrasound diagnostic apparatus and a control method for an ultrasound diagnostic apparatus according to an embodiment of the present invention will be described in detail based on a preferred embodiment illustrated in the accompanying drawings.

Figure 1:
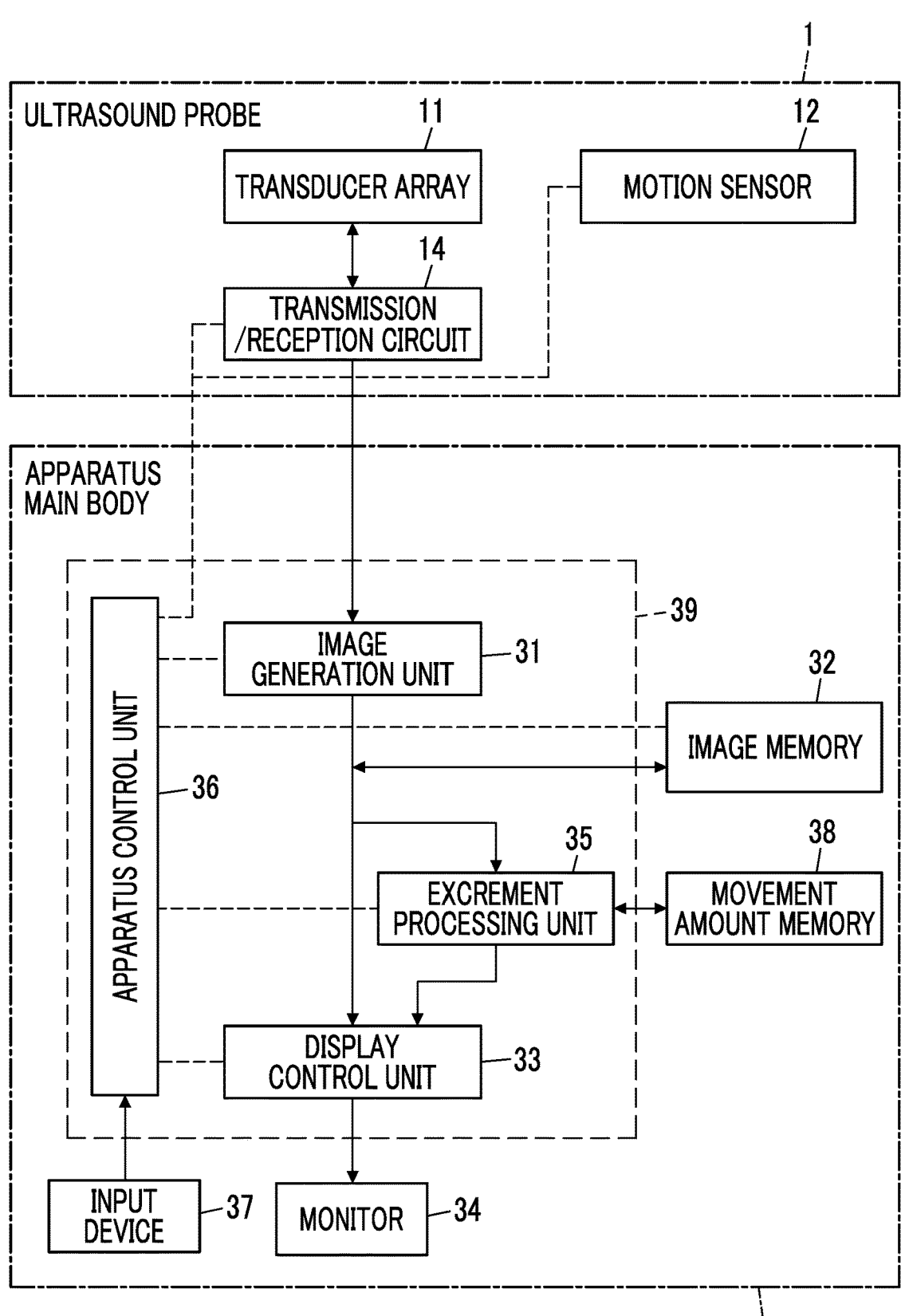
FIG. 1 is a block diagram of an embodiment illustrating a configuration of an ultrasound diagnostic apparatus of the present invention.

FIG. 1 is a block diagram illustrating a configuration of an ultrasound diagnostic apparatus according to an embodiment of the present invention. The ultrasound diagnostic apparatus illustrated in FIG. 1 is a stationary ultrasound diagnostic apparatus, and comprises an ultrasound probe 1, and an apparatus main body 3 connected to the ultrasound probe 1.

The ultrasound probe 1 scans an examination area of a subject with an ultrasound beam and outputs a sound ray signal corresponding to an ultrasound image of the examination area. As illustrated in FIG. 1, the ultrasound probe 1 comprises a transducer array 11, a transmission/reception circuit 14, and a motion sensor 12. The transducer array 11 and the transmission/reception circuit 14 are bidirectionally connected to each other. In addition, the transmission/reception circuit 14 and the motion sensor 15 are connected to an apparatus control unit 36 of the apparatus main body 3 to be described below.

The transducer array 11 includes a plurality of ultrasound transducers arranged one-dimensionally or two-dimensionally. In response to a drive signal supplied from the transmission/reception circuit 14, each of the transducers transmits an ultrasound wave, receives a reflected wave from the subject, and outputs an analog reception signal.

For example, each transducer is configured by using an element in which electrodes are formed at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

Figure 2:
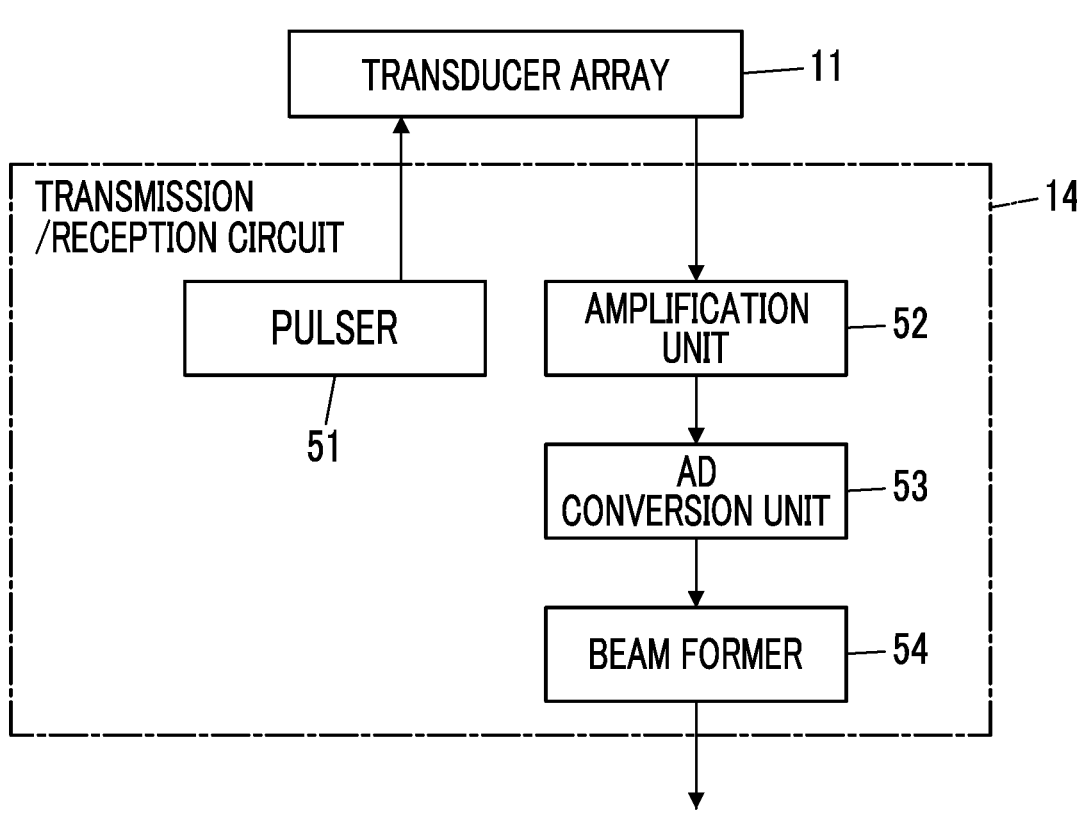
FIG. 2 is a block diagram of an embodiment illustrating a configuration of a transmission/reception circuit.

Under a control of the apparatus control unit 36, the transmission/reception circuit 14 causes the transducer array 11 to transmit an ultrasound wave, and performs reception focusing processing on the reception signal output from the transducer array 11 that receives an ultrasound echo. Thereby, a sound ray signal is generated. As illustrated in FIG. 2, the transmission/reception circuit 14 includes a pulser 51 connected to the transducer array 11, and an amplification unit 52, an analog-to-digital (AD) conversion unit 53, and a beam former 54 that are sequentially connected in series from the transducer array 11.

The pulser 51 includes, for example, a plurality of pulse generators. The pulser 51 adjusts a delay amount of each drive signal such that ultrasound waves transmitted from the plurality of transducers of the transducer array 11 form an ultrasound beam based on a transmission delay pattern selected by the apparatus control unit 36, and supplies the drive signals to the plurality of transducers. In this way, in a case where a voltage having a pulse shape or a continuous wave shape is applied to the electrodes of the transducers of the transducer array 11, the piezoelectric body expands and contracts. Thereby, ultrasound waves having a pulse shape or a continuous wave shape are generated from each transducer, and thus an ultrasound beam is formed from a composite wave of these ultrasound waves.

The transmitted ultrasound beam is reflected by, for example, a target such as a region of the subject, and propagates toward the transducer array 11 of the ultrasound probe 1. In a case where the ultrasound echo propagating toward the transducer array 11 in this way is received, each transducer of the transducer array 11 expands and contracts, and thus the reception signal that is an electric signal is generated. The reception signal is output to the amplification unit 52.

The amplification unit 52 amplifies the signals input from each transducer of the transducer array 11, and transmits the amplified signals to the AD conversion unit 53. The AD conversion unit 53 converts the analog signal transmitted from the amplification unit 52 into digital reception data, and outputs the reception data to the beam former 54.

The beam former 54 performs so-called reception focusing processing in which addition is performed by giving delays to each of pieces of the reception data converted by the AD conversion unit 53 according to a sound speed or a sound speed distribution which is set based on a reception delay pattern selected by the apparatus control unit 36. By this reception focusing processing, each of pieces of reception data converted by the AD conversion unit 53 is phase-added, and a sound ray signal in which the focus of the ultrasound echo is narrowed down is generated.

The motion sensor 12 detects the motion of the ultrasound probe 1.

Next, the apparatus main body 3 generates an ultrasound image of the examination area of the subject based on the sound ray signal generated by the ultrasound probe 1, and displays the ultrasound image of the examination area of the subject. As illustrated in FIG. 1, the apparatus main body 3 comprises an image generation unit 31, an image memory 32, an excrement processing unit 35, a movement amount memory 38, a display control unit 33, a monitor (display unit) 34, an input device 37, and the apparatus control unit 36.

The image generation unit 31 is connected to the transmission/reception circuit 14, and the display control unit 33 and the monitor 34 are sequentially connected to the image generation unit 31. In addition, each of the image memory 32 and the excrement processing unit 35 is connected to the image generation unit 31, and the display control unit 33 is connected to the image memory 32 and the excrement processing unit 35. The excrement processing unit 35 is bidirectionally connected to the movement amount memory 38. The image generation unit 31, the display control unit 33, the image memory 32, and the excrement processing unit 35 are connected to the apparatus control unit 36, and the apparatus control unit 36 is connected to the input device 37.

Figure 3:
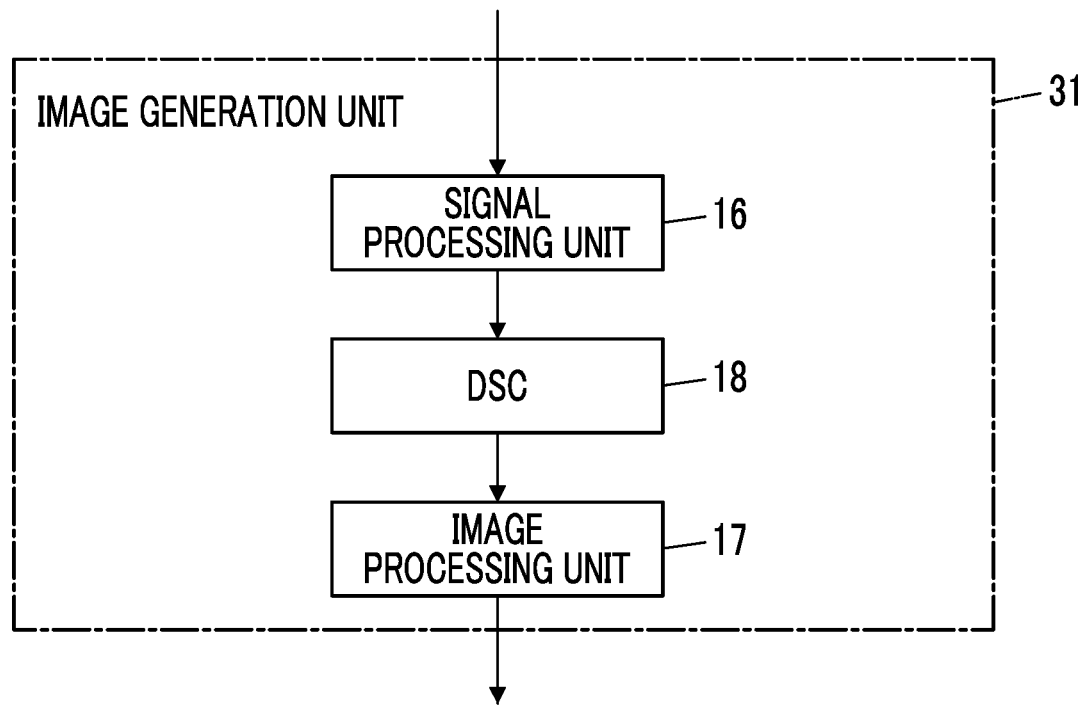
FIG. 3 is a block diagram of an embodiment illustrating a configuration of an image generation unit.

The image generation unit 31 generates an ultrasound image (ultrasound image signal) of the examination area of the subject, based on the reception signal obtained by scanning the examination area of the subject with the ultrasound beams by using the ultrasound probe 1 (more precisely, the transducer array 11), in other words, based on the sound ray signal generated from the reception signal by the transmission/reception circuit 14, under a control of the apparatus control unit 36. As illustrated in FIG. 3, the image generation unit 31 has a configuration in which a signal processing unit 16, a digital scan converter (DSC) 18, and an image processing unit 17 are sequentially connected in series.

The signal processing unit 16 generates image information data corresponding to the ultrasound image based on the sound ray signal generated by the transmission/reception circuit 14. More specifically, the signal processing unit 16 generates the image information data representing tomographic image information related to tissues inside the subject, by performing signal processing, for example, processing of correcting attenuation of the sound ray signal generated by the beam former 54 of the transmission/reception circuit 14, the attenuation being caused by a propagation distance according to a depth of the reflection position of the ultrasound wave, and then performing envelope detection processing.

The DSC 18 raster-converts the image information data generated by the signal processing unit 16 into an image signal according to a normal television signal scanning method.

The image processing unit 17 generates an ultrasound image (ultrasound image signal) by performing, on the image signal input from the DSC 18, various kinds of image processing such as brightness correction, gradation correction, sharpness correction, image size correction, refresh rate correction, scanning frequency correction, and color correction according to a display format of the monitor 34, and outputs the ultrasound image obtained by performing the image processing to the image memory 32, the excrement processing unit 35, and the display control unit 33.

The image memory 32 is a memory that stores ultrasound images (ultrasound image signals) of a series of a plurality of frames generated for each examination by the image generation unit 31, under a control of the apparatus control unit 36.

The movement amount memory 38 is a memory that stores the movement amount of the ultrasound probe 1, for example, for each frame of the ultrasound images, under a control of the excrement processing unit 35.

The display control unit 33 displays various kinds of information on the monitor 34 under a control of the apparatus control unit 36. For example, the display control unit 33 performs predetermined processing on the ultrasound image generated by the image generation unit 31 or the ultrasound image stored in the image memory 32, and displays the processed ultrasound image on the monitor 34.

The monitor 34 displays various kinds of information under a control of the display control unit 33. The monitor 34 displays, for example, an ultrasound image or the like. Examples of the monitor 34 include a liquid crystal display (LCD), an organic electro-luminescence (EL) display, and the like.

The input device 37 receives various instructions input from the user (examiner) of the ultrasound diagnostic apparatus. The input device 37 is not particularly limited, and includes various buttons, a voice input device that inputs various instructions using voice recognition, a touch panel that allows a user to input various instructions by performing a touch operation on a graphical user interface (GUI) screen displayed on the monitor 34, and the like.

The apparatus control unit 36 controls the ultrasound probe 1 and each unit of the apparatus main body 3 based on a program stored in advance and an instruction or the like of the user that is input from the input device 37.

Figure 4:
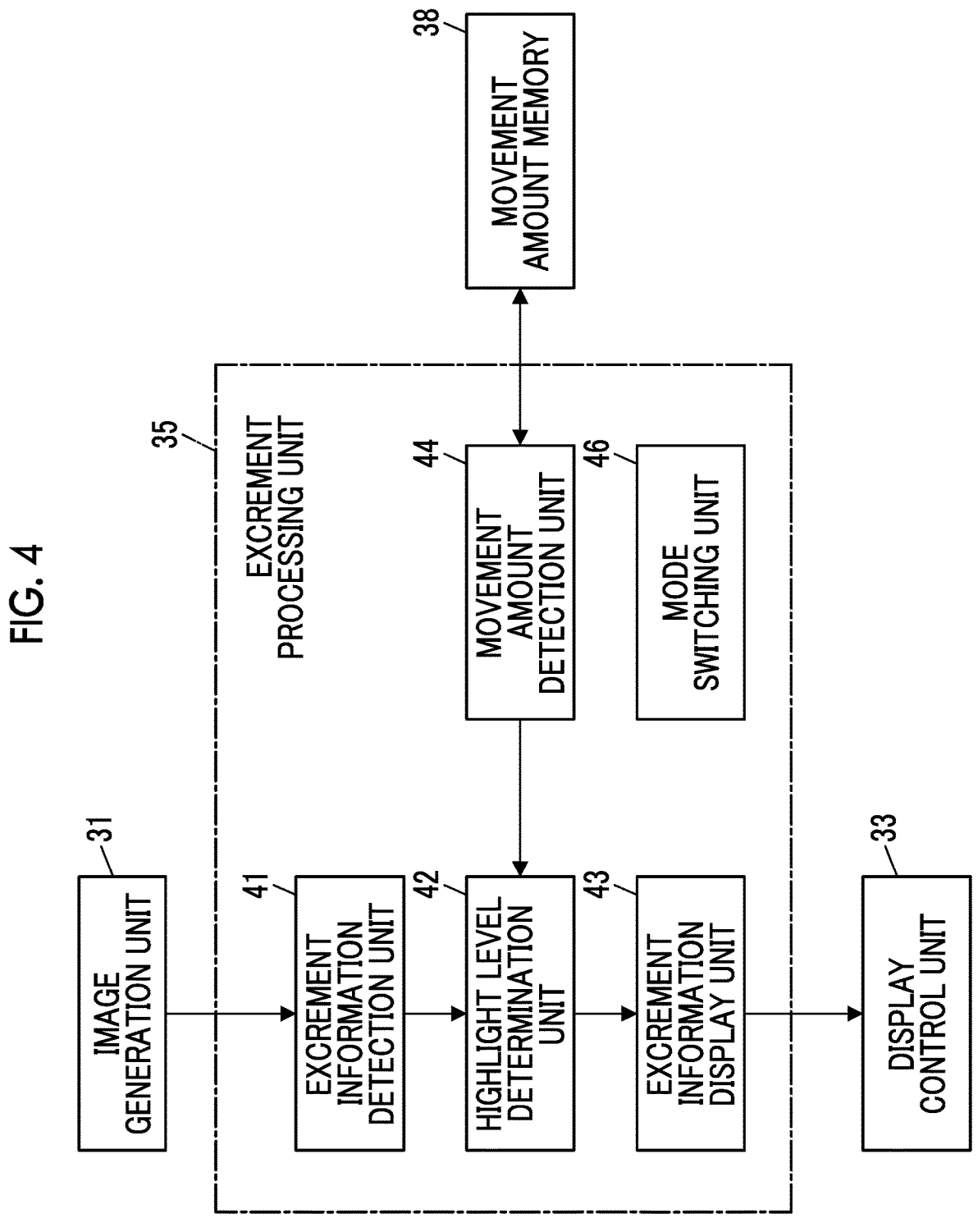
FIG. 4 is a block diagram of an embodiment illustrating a configuration of an excrement processing unit.

The excrement processing unit 35 performs various kinds of processing for highlight-displaying an excrement region in the ultrasound image, under a control of the apparatus control unit 36. As illustrated in FIG. 4, the excrement processing unit 35 includes an excrement information detection unit 41, a movement amount detection unit 44, a highlight level determination unit 42, an excrement information display unit 43, and a mode switching unit 46.

The excrement information detection unit 41 is connected to the image generation unit 31. The highlight level determination unit 42 is connected to each of the excrement information detection unit 41 and the movement amount detection unit 44. The excrement information display unit 43 is connected to the highlight level determination unit 42, and the display control unit 33 is connected to the excrement information display unit 43. The movement amount detection unit 44 is bidirectionally connected to the movement amount memory 38. Although not illustrated, each unit of the excrement processing unit 35 is connected to the mode switching unit 46.

The excrement information detection unit 41 detects various types of information related to excrements from the ultrasound image by analyzing the ultrasound image. The excrement information detection unit 41 performs, for example, detection processing for detecting an excrement region, which is a region where excrement is present, from the ultrasound image. The excrement information detection unit 41 performs, in addition to the detection of the excrement region, detection processing for detecting an excrement property of the excrement region from the ultrasound image, as a result of the detection processing of the excrement region.

A detection method of the excrement region is not particularly limited. For example, the excrement information detection unit 41 can detect an excrement region from an ultrasound image by using at least one of template matching, machine learning using image feature amounts, or a deep learning model.

In a case of detecting an excrement region from an ultrasound image by using template matching, the excrement information detection unit 41 prepares a plurality of templates having different sizes, shapes, textures, and the like in a region of interest, and performs raster scanning of the ultrasound image by using each of the plurality of templates. Thereby, a region of which a correlation value with the template is equal to or higher than a predetermined threshold value is detected as an excrement region.

In a case of detecting an excrement region from an ultrasound image by using machine learning using image feature amounts, the excrement information detection unit 41 prepares a plurality of training images including an anatomical structure and an excrement region, converts a region of interest into a feature amount vector (image quantization), and performs machine learning using a machine learning algorithm such as adaptive boosting (Adaboost) or support vector machine (SVM). Thereby, an excrement region is detected from the ultrasound image.

In a case of detecting an excrement region from an ultrasound image by using a deep learning model, the excrement information detection unit 41 prepares a large number of training images including an anatomical structure and an excrement region, creates a deep learning model obtained by learning, for the large number of training images, a relationship between the training image and the excrement region in the training image by using the large number of the training images, and detects an excrement region from the ultrasound image by using the deep learning model.

In a case of detecting an excrement region from an ultrasound image by using the deep learning model, the excrement information detection unit 41 may detect only an excrement region from an ultrasound image by using the deep learning model, or detect an excrement region and a probability that the excrement region is a region of excrement.

In a case of detecting only an excrement region, the excrement information detection unit 41 detects the excrement region as a rectangular region, for example, by using the deep learning model.

In a case of detecting an excrement region and a probability that the excrement region is a region of excrement, the excrement information detection unit 41 detects an excrement region as a rectangular region for each frame of the ultrasound images by using, for example, the deep learning model, and detects a position of the excrement region and a probability that the excrement region is a region of excrement. In addition, the excrement information detection unit 41 detects whether or not the excrement region is a region where excrement is actually present by comparing a statistic value of the probabilities of the ultrasound images of the plurality of frames, for example, an average value, a weighted average value, a median value, or the like with a threshold value. The excrement information detection unit 41 detects that an excrement region is a region of excrement, for example, in a case where a statistic value of the probabilities that the excrement region is a region where excrement is present is equal to or higher than a threshold value.

Alternatively, the excrement information detection unit 41 may detect a probability that a pixel is a pixel of excrement for each pixel of the ultrasound image by using the deep learning model. In this case, the excrement information detection unit 41 detects a probability that a pixel is a pixel of excrement for each frame of the ultrasound images and for each pixel of the ultrasound image, by using the deep learning model, and detects whether or not a pixel is a pixel of excrement by comparing a probability that a pixel is a pixel of excrement with a threshold value. The excrement information detection unit 41 detects that a pixel is a pixel of excrement, for example, in a case where the probability is equal to or higher than the threshold value. In addition, the excrement information detection unit 41 detects, as an excrement region, a collection (cluster) of a plurality of pixels that are detected as pixels of excrement.

As described above, in a case of detecting excrement regions from the ultrasound images of the plurality of frames, it is desirable that the excrement information detection unit 41 performs processing on the identical excrement region by performing identity determination to determine whether or not the excrement regions in the ultrasound images of the adjacent frames are the identical excrement region.

A method of performing identity determination is not particularly limited. For example, the excrement information detection unit 41 can determine whether or not the excrement regions are the same by obtaining an evaluation index based on an intersection over union (IoU) of the excrement regions in the ultrasound images of the adjacent frames, that is, a degree of superimposition of the excrement regions in the ultrasound images of the adjacent frames, and comparing the evaluation index with a threshold value. The excrement information detection unit 41 determines that the excrement regions are the same, for example, in a case where the evaluation index is equal to or higher than the threshold value.

A method of detecting an excrement property is not particularly limited. For example, the excrement information detection unit 41 can detect an excrement property of the excrement region, for example, based on a brightness value of the excrement region or using the deep learning model.

In a case of detecting an excrement property based on a brightness value of an excrement region, for example, the excrement information detection unit 41 detects an excrement region from the ultrasound image, detects a statistic value of brightness in the excrement region, for example, an average value, a weighted average value, a median value, or the like for each frame of the ultrasound images, obtains a first comparison result by comparing the statistic value of the brightness in the excrement region with a threshold value, and detects an excrement property based on the first comparison result in the ultrasound images of one frame or a plurality of frames. For example, the excrement information detection unit 41 detects that the excrement is hard in a case where the statistic value of the brightness is equal to or higher than a first threshold value, detects that the excrement is normal in a case where the statistic value of the brightness is equal to or higher than a second threshold value lower than the first threshold value and is lower than the first threshold value, and detects that the excrement is soft in a case where the statistic value of the brightness is lower than the second threshold value.

Alternatively, the excrement information detection unit 41 may detect an excrement region from the ultrasound image for each frame of the ultrasound images, detect a brightness ratio between a statistic value of brightness in the excrement region and a statistic value of brightness in a predetermined region around the excrement region, obtain a second comparison result by comparing the brightness ratio and a threshold value, and detect an excrement property based on the second comparison result in the ultrasound images of one frame or a plurality of frames. Similarly, the excrement information detection unit 41 detects that the excrement is hard in a case where the brightness ratio is equal to or higher than a first threshold value, detects that the excrement is normal in a case where the brightness ratio is equal to or higher than a second threshold value lower than the first threshold value and is lower than the first threshold value, and detects that the excrement is soft in a case where the brightness ratio is lower than the second threshold value.

In a case of detecting an excrement property by using the deep learning model, the excrement information detection unit 41 may detect, as the excrement property, a probability that the excrement region is included in each class of excrement properties, for example, a probability that the excrement is hard, soft, normal, or background, or may detect a probability that a pixel is included in each class of excrement properties for each pixel of the ultrasound image.

In a case of detecting a probability that the excrement region is included in each class of the excrement properties, for example, the excrement information detection unit 41 detects an excrement region as a rectangular region by using the deep learning model, and detects a probability that the excrement region is included in each class of the excrement properties. In addition, the excrement information detection unit 41 detects a class having a highest probability among the classes of the excrement properties, as the excrement property of the excrement region.

In a case of detecting, for each pixel of the ultrasound image, a probability that the pixel is included in each class of the excrement properties, for example, the excrement information detection unit 41 detects, for each pixel of the ultrasound image, a probability that the pixel is included in each class of the excrement properties by using a deep learning model, and detects a class having a highest probability among the classes of the excrement properties, as a class of the pixel. Subsequently, the excrement information detection unit 41 detects, as an excrement region, a collection (cluster) of a plurality of pixels detected as pixels of excrement based on the classes of the pixels. In this case, a plurality of pixels having different classes may be mixed in one excrement region. Accordingly, the excrement information detection unit 41 obtains a total area of the classes for each class of the excrement properties, and detects a class having a largest total area, as the excrement property of the excrement region.

The movement amount detection unit 44 detects a movement amount of the ultrasound probe 1 in a case where scanning is performed.

A method of detecting the movement amount is not particularly limited. For example, the movement amount detection unit 44 can detect the movement amount of the ultrasound probe 1 based on at least one of an analysis result of the ultrasound image or a movement detection result obtained by the motion sensor 12 provided in the ultrasound probe 1.

In a case where an excrement region is detected from the ultrasound image as a result of the detection processing of the excrement region, the highlight level determination unit 42 determines (changes) a highlight level of the excrement region when performing highlight-display of the excrement region, based on a determination condition for determining (changing) a highlight level of the excrement region.

The determination condition of the highlight level is not particularly limited. For example, at least one of a movement amount of the ultrasound probe 1, a continuous display time of the identical excrement region (the number of frames in which the identical excrement region is continuously displayed), or an area of the excrement region can be used.

Conversion from each of the movement amount of the ultrasound probe 1, the continuous display time of the identical excrement region, and the area of the excrement region into the highlight level of the excrement region can be performed by, for example, preparing a lookup table (LUT) or a conversion equation in advance and using the LUT or the conversion equation.

In a case where the determination condition of the highlight level is the movement amount of the ultrasound probe 1, the highlight level determination unit 42 determines a highlight level of the excrement region based on the movement amount of the ultrasound probe 1.

In a case where the movement amount of the ultrasound probe 1 is large, it is considered that the user is searching for excrement. Therefore, the highlight level determination unit 42 increases the highlight level of the excrement region as the movement amount of the ultrasound probe 1 increases in order to make it easier for the user to recognize an excrement region.

On the other hand, in a case where the movement amount of the ultrasound probe 1 is small, it is considered that the user recognizes an excrement region. Therefore, the highlight level determination unit 42 decreases the highlight level of the excrement region as the movement amount of the ultrasound probe 1 decreases so as not to interfere with the user's interpretation of the ultrasound image.

In a case where the determination condition of the highlight level is the continuous display time of the identical excrement region, the highlight level determination unit 42 performs the above-described identity determination of the excrement region, and determines a highlight level of the excrement region based on the continuous display time of the excrement region determined to be the same.

A fact that the continuous display time of the excrement region is long means that the excrement regions of the adjacent frames do not move and a time for which the excrement regions of the adjacent frames are determined to be the same is long (the number of the frames is large), that is, that a time for which the movement amount of the ultrasound probe 1 is small is long.

In a case where the continuous display time of the excrement region is short, it is considered that there is a high possibility that the user does not yet sufficiently recognize the excrement region. Therefore, the highlight level determination unit 42 increases the highlight level of the excrement region according to the continuous display time of the excrement region, as the continuous display time of the excrement region is shorter, such that the user can easily recognize the excrement region.

On the other hand, in a case where the continuous display time of the excrement region is long, it is considered that the excrement region is already recognized by the user. Therefore, the highlight level determination unit 42 decreases the highlight level of the excrement region according to the continuous display time of the excrement region, as the continuous display time of the excrement region is longer, so as not to interfere with the user's interpretation of the ultrasound image.

In a case where the determination condition of the highlight level is the area of the excrement region, the highlight level determination unit 42 determines a highlight level of the excrement region based on the area of the excrement region.

In a case where the area of the excrement region is small, there is a probability that the user may overlook the excrement region. Therefore, the highlight level determination unit 42 increases the highlight level of the excrement region according to the area of the excrement region as the area of the excrement region is smaller, such that the user can easily recognize the excrement region.

On the other hand, in a case where the area of the excrement region is large, the user can easily recognize the excrement region. Therefore, the highlight level determination unit 42 decreases the highlight level of the excrement region according to the area of the excrement region, as the area of the excrement region is larger, so as not to interfere with the user's interpretation of the ultrasound image.

The highlight level determination unit 42 can also change the highlight level of the excrement region according to an instruction from the user, regardless of the determination condition of the highlight level.

The excrement information display unit 43 displays various types of information related to the excrement on the monitor 34 under a control of the display control unit 33. For example, the excrement information display unit 43 highlight-displays the excrement region in the ultrasound image displayed on the monitor 34 according to the highlight level determined (changed) by the highlight level determination unit 42.

A method of highlight-displaying the excrement region is not particularly limited. For example, the excrement information display unit 43 may create a contour line of the excrement region by detecting a contour of the excrement region, and display the contour line by superimposing the contour line on the contour of the excrement region. In addition, the excrement information display unit 43 may create a mask obtained by coloring and filling the inside of the excrement region with a predetermined display color, and display the mask by superimposing the mask on the excrement region. Further, the excrement information display unit 43 may highlight-display the excrement region by using both the mask and the contour line.

The ultrasound diagnostic apparatus has at least two operation modes among a first operation mode in which the excrement region is not highlight-displayed, a second operation mode in which the excrement region is highlight-displayed at a predetermined highlight level regardless of the determination condition of the highlight level, and a third operation mode in which a highlight level is determined (changed) based on the determination condition of the highlight level and the excrement region is highlight-displayed.

The mode switching unit 46 switches the operation mode to one operation mode of at least two operation modes described above in response to an instruction input from the user by using, for example, a GUI, voice recognition, or the like.

The image generation unit 31, the excrement processing unit 35, the display control unit 33, and the apparatus control unit 36 are configured by a processor 39.

Figure 5:
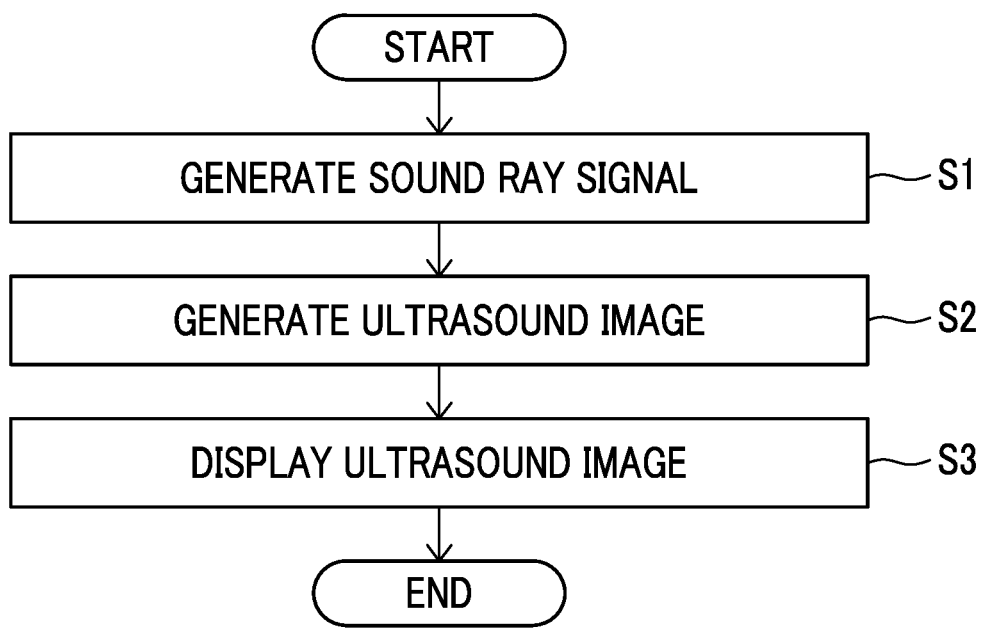
FIG. 5 is a flowchart of an embodiment illustrating an operation of the ultrasound diagnostic apparatus in a first operation mode.

Next, an operation of the ultrasound diagnostic apparatus in the first operation mode will be described with reference to a flowchart of FIG. 5.

In this case, first, in a state where the ultrasound probe 1 is in contact with the examination area of the subject, under the control of the apparatus control unit 36, transmission of the ultrasound waves is started by the transmission/reception circuit 14, and the sound ray signal is generated (step S1).

That is, the ultrasound beams are transmitted to the examination area of the subject from the plurality of transducers of the transducer array 11 in accordance with the drive signal from the pulser 51.

The ultrasound echoes from the examination area based on the ultrasound beams transmitted from the pulser 51 are received by each transducer of the transducer array 11, and the reception signal as an analog signal is output from each transducer of the transducer array 11 that receives the ultrasound echoes.

The reception signal output from each transducer of the transducer array 11 is amplified by the amplification unit 52, and is subjected to AD conversion by the AD conversion unit 53. Thereby, the reception data is acquired.

By performing the reception focusing processing on the reception data by the beam former 54, the sound ray signal is generated.

Next, under the control of the apparatus control unit 36, the ultrasound image (ultrasound image signal) of the examination area of the subject is generated by the image generation unit 31 based on the sound ray signal generated by the beam former 54 of the transmission/reception circuit 14 (step S2).

That is, the sound ray signal generated by the beam former 54 is subjected to various kinds of signal processing by the signal processing unit 16, and the image information data representing tomographic image information related to tissues inside the subject is generated.

The image information data generated by the signal processing unit 16 is raster-converted by the DSC 18, and is further subjected to various kinds of image processing by the image processing unit 17. Thereby, the ultrasound image (ultrasound image signal) is generated.

The ultrasound image generated by the image processing unit 17 is stored in the image memory 32.

Next, under the control of the apparatus control unit 36, predetermined processing is performed on the ultrasound image generated by the image processing unit 17 or the ultrasound image stored in the image memory 32 by the display control unit 33, and the processed ultrasound image is displayed on the monitor 34 (step S3).

Next, an operation of the ultrasound diagnostic apparatus in the second operation mode will be described with reference to a flowchart illustrated in FIG. 6.

In this case, first, the image generation unit 31 generates an ultrasound image for each frame of the ultrasound images, and the ultrasound image is stored in the image memory 32 (step S11).

Subsequently, the excrement information detection unit 41 analyzes the ultrasound image, and performs detection processing for detecting an excrement region from the ultrasound image (step S12).

As a result, in a case where an excrement region is not detected from the ultrasound image (No in step S13), the process returns to step S11, and detection processing of an excrement region is repeatedly performed until an excrement region is detected from the ultrasound image.

On the other hand, in a case where an excrement region is detected from the ultrasound image (Yes in step S13), the highlight level determination unit 42 determines a highlight level to be a predetermined highlight level regardless of the determination condition of the highlight level (step S14). That is, in the second operation mode, the highlight level determination unit 42 does not change the highlight level of the excrement region from the predetermined highlight level even in a case where the determination condition of the highlight level is changed.

In addition, under the control of the display control unit 33, the excrement information display unit 43 highlight-displays the excrement region in the ultrasound image displayed on the monitor 34 at the predetermined highlight level (step S15).

Thereafter, the process returns to step S11, and the operation described above is repeated for each frame of the ultrasound images.

As described above, in the ultrasound diagnostic apparatus in the second operation mode, the excrement region is highlight-displayed in the ultrasound image displayed on the monitor 34. Therefore, the user can easily recognize the excrement region in the ultrasound image.

Figure 7:
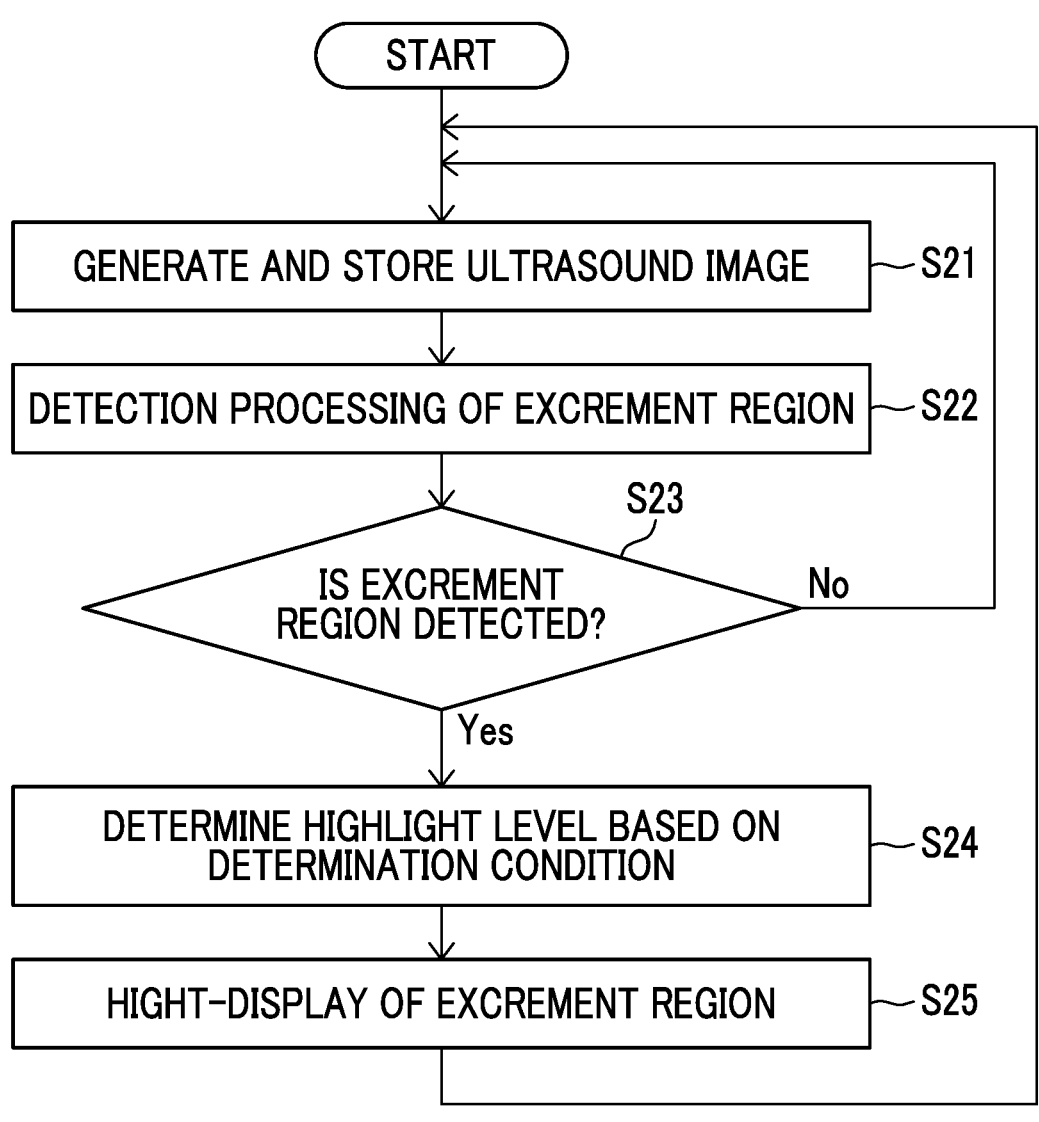
FIG. 7 is a flowchart of an embodiment illustrating an operation of the ultrasound diagnostic apparatus in a third operation mode.

Next, an operation of the ultrasound diagnostic apparatus in the third operation mode will be described with reference to a flowchart illustrated in FIG. 7.

Figure 6:
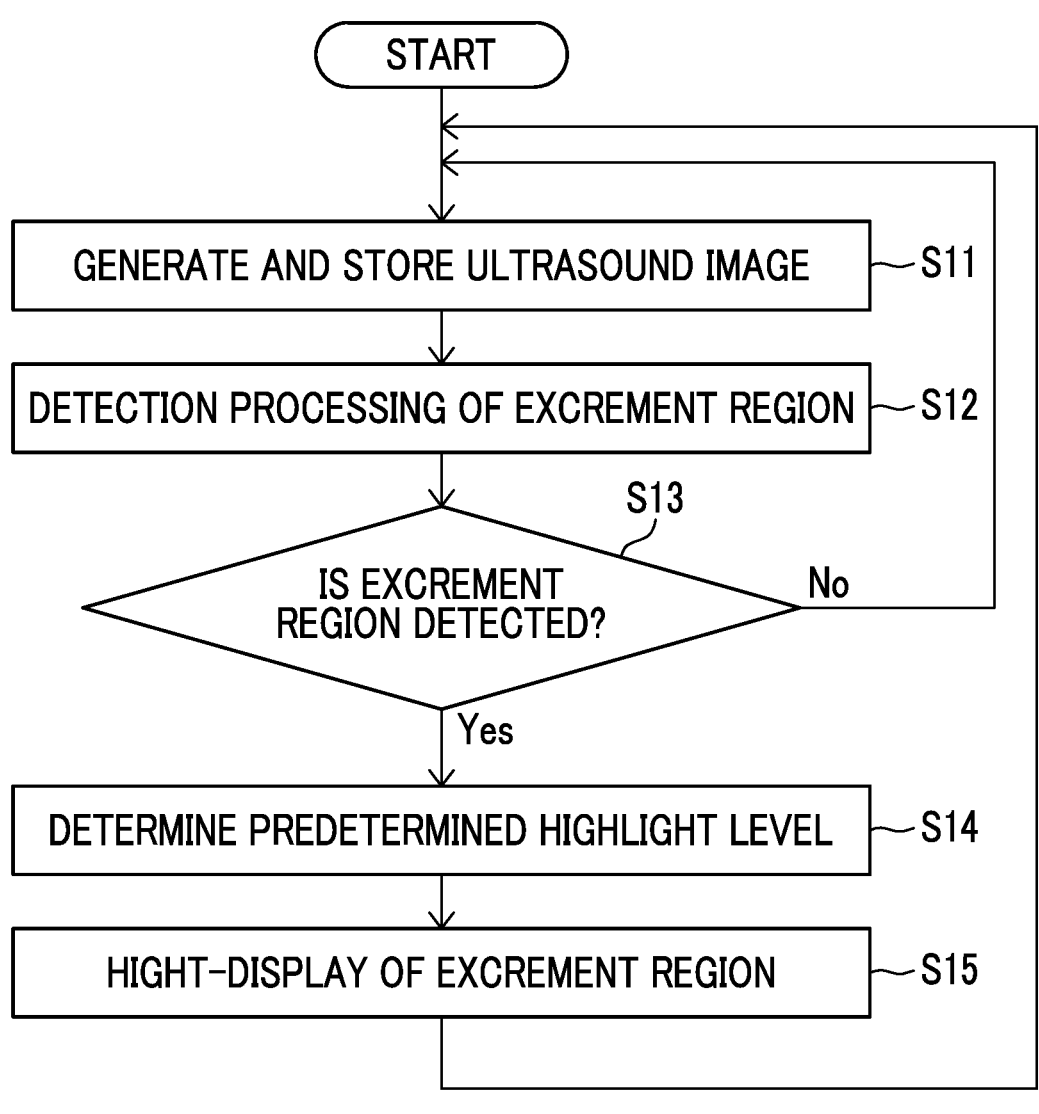
FIG. 6 is a flowchart of an embodiment illustrating an operation of the ultrasound diagnostic apparatus in a second operation mode.

In this case, the operation from step S21 to step S23 is the same as the operation from step S11 to step S13 in the flowchart of FIG. 6.

As a result of detection processing of an excrement region, in a case where an excrement region is not detected from the ultrasound image (No in step S23), the process returns to step S21, and detection processing of an excrement region is repeatedly performed until an excrement region is detected from the ultrasound image.

On the other hand, in a case where an excrement region is detected from the ultrasound image (Yes in step S23), the highlight level determination unit 42 determines a highlight level based on the determination condition of the highlight level (step S24). That is, in the third operation mode, the highlight level determination unit 42 changes the highlight level of the excrement region based on the determination condition of the highlight level in a case where the determination condition of the highlight level is changed.

In addition, under the control of the display control unit 33, the excrement information display unit 43 highlight-displays the excrement region in the ultrasound image displayed on the monitor 34 according to the highlight level determined (changed) based on the determination condition of the highlight level (step S25).

Thereafter, the process returns to step S21, and the operation described above is repeated for each frame of the ultrasound images.

As described above, in the ultrasound diagnostic apparatus in the third operation mode, the excrement region is highlight-displayed in the ultrasound image displayed on the monitor 34 according to the highlight level determined (changed) based on the determination condition of the highlight level. Therefore, the user can easily recognize the excrement region in the ultrasound image in a case where the highlight level is determined to be higher according to the determination condition, and the user can perform interpretation of the ultrasound image without interference by the highlight-display in a case where the highlight level is determined to be lower.

Next, a method of detecting the movement amount of the ultrasound probe 1 based on the analysis result of the ultrasound image will be described with a specific example.

For example, the movement amount detection unit 44 can obtain, for each frame of the ultrasound images, a correlation value between the ultrasound images of the adjacent frames, that is, a correlation value between the ultrasound image of the current frame and the ultrasound image of the previous frame that is previous to the current frame by one frame, as the movement amount of the ultrasound image between the adjacent frames, that is, the movement amount of the ultrasound probe 1. The movement amount detection unit 44 detects that the movement amount of the ultrasound probe 1 is smaller as the correlation value is larger and the movement amount of the ultrasound probe 1 is larger as the correlation value is smaller. That is, a magnitude relationship between the correlation value and the movement amount of the ultrasound probe 1 is an inverse relationship.

In this case, assuming that the current frame is n, the movement amount detection unit 44 obtains a correlation value between the ultrasound image of an n-th frame and the ultrasound image of an (n−1)-th frame.

A method of calculating the correlation value is not particularly limited. For example, the correlation value can be calculated by performing a normalized cross-correlation calculation. Further, as the correlation value, an optical flow of the ultrasound image between the adjacent frames may be calculated.

Alternatively, the movement amount detection unit 44 may obtain, for each frame of the ultrasound images, a correlation value between the ultrasound image of the current frame and the ultrasound image of the previous frame that is previous to the ultrasound image of the current frame by a predetermined number of frames, for example, by five frames, as the movement amount of the ultrasound probe 1.

In this case, assuming that the current frame is n, the movement amount detection unit 44 obtains a correlation value between the ultrasound image of an n-th frame and the ultrasound image of an (n−5)-th frame.

Depending on the frame rate, the correlation value between the ultrasound images of the adjacent frames may be too large. As a result, it may be difficult to accurately obtain the movement amount of the ultrasound probe 1. In contrast, it is possible to more accurately obtain the movement amount of the ultrasound probe 1 by obtaining the correlation value between the ultrasound images of the frames separated by a predetermined number of frames.

The movement amount detection unit 44 may obtain, for each frame of the ultrasound images, a degree of superimposition between the excrement region of the ultrasound image of the current frame and the excrement region of the ultrasound image of the previous frame that is previous to the current frame by one frame, as the movement amount of the ultrasound probe 1. The movement amount detection unit 44 detects that the movement amount of the ultrasound probe 1 is smaller as the degree of superimposition between the excrement regions is larger and the movement amount of the ultrasound probe 1 is larger as the degree of superimposition between the excrement regions is smaller.

A method of calculating the degree of superimposition is not particularly limited. For example, the movement amount detection unit 44 can obtain the evaluation index based on the IoU described above, as the degree of superimposition between the excrement regions in the ultrasound images of the frames. The correlation value between the excrement regions and the degree of superimposition between the excrement regions can be equally treated as the movement amount of the ultrasound probe 1.

Further, the movement amount detection unit 44 may obtain, for each frame of the ultrasound images, the movement amount between the ultrasound image of the current frame and the ultrasound image of the previous frame that is previous to the current frame by one frame, as the movement amount of the ultrasound image of the current frame, and obtain a statistic value obtained from a movement amount group consisting of the movement amount of the ultrasound image of the current frame and movement amounts of the ultrasound images of a predetermined number of previous frames, for example, a statistic value obtained from a group of movement amounts of the ultrasound images of 10 frames, as the movement amount of the ultrasound probe 1.

In this case, assuming that the current frame is n, the movement amount detection unit 44 obtains the movement amount between the ultrasound image of an n-th frame and the ultrasound image of an (n−1)-th frame, and obtains a statistic value from a group of movement amounts of the ultrasound images for 10 frames from the n-th frame to the (n−9)-th frame.

In a case of obtaining the movement amount between the ultrasound images of the adjacent frames and changing the highlight level of the excrement region, for example, transparency of a display color of the excrement region, the highlight level of the excrement region is frequently changed, and as a result, it may be difficult to recognize the excrement region. In contrast, by obtaining, as the movement amount of the ultrasound probe 1, a statistic value obtained from a group of movement amounts of the ultrasound images of the plurality of frames, it is possible to more accurately calculate the movement amount of the ultrasound probe 1, and it is possible to prevent the highlight level of the excrement region from being frequently changed.

The statistic value is not particularly limited. For example, an average value obtained from the movement amount group, a weighted average value obtained from the movement amount group by using a weight increasing from the past to the present, a median value obtained from the movement amount group, or the like can be used as an example.

In a case where a statistic value is obtained from the group of the movement amounts of the ultrasound images of the plurality of frames, movement amounts may be obtained for each frame of the ultrasound images regardless of whether or not the excrement region is detected, and a statistic value may be obtained from a group of the movement amounts of the ultrasound images of the plurality of frames.

Figure 8:
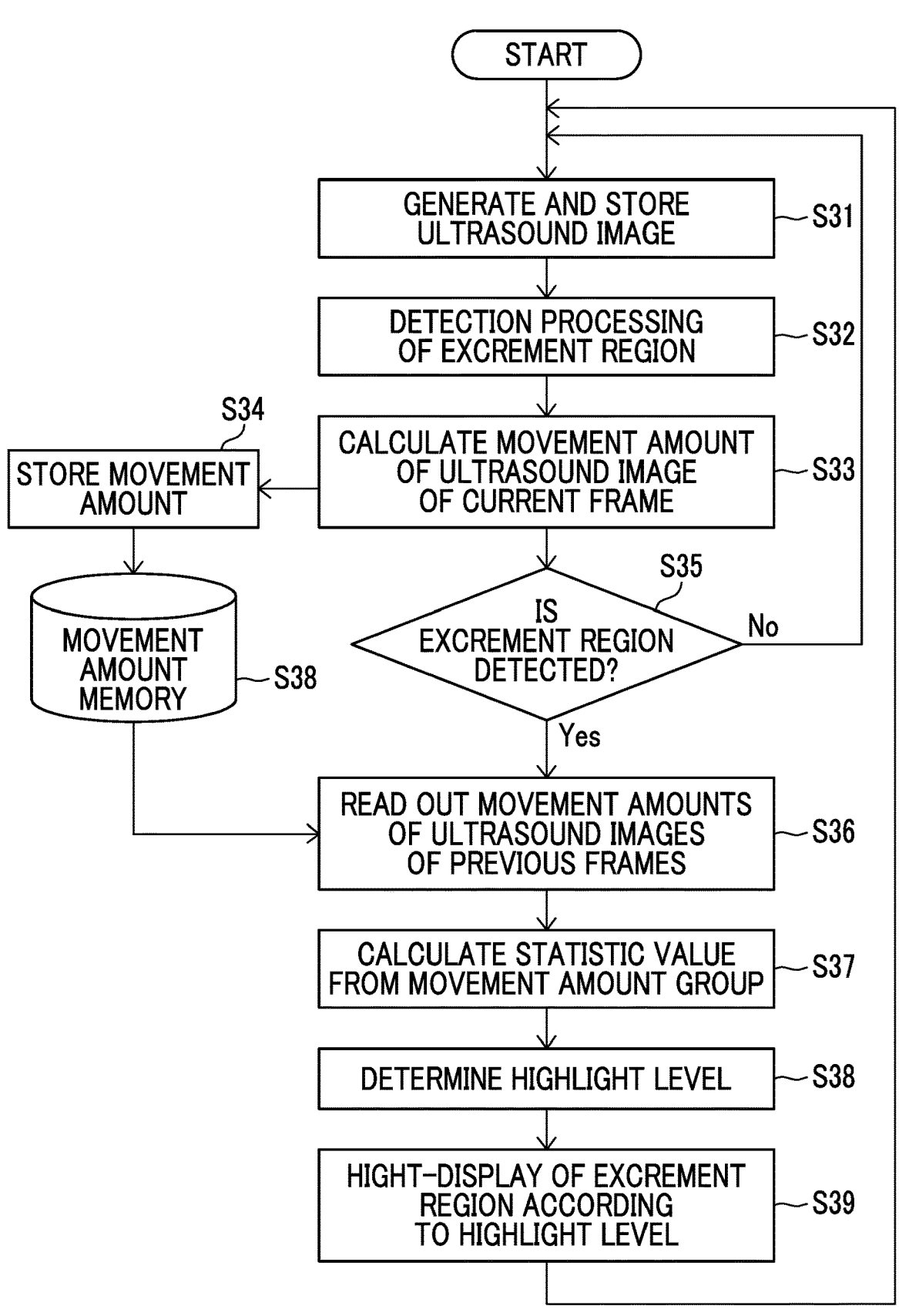
FIG. 8 is a flowchart of an embodiment illustrating an operation of the ultrasound diagnostic apparatus in a case of obtaining a statistic value from a group of movement amounts of ultrasound images of a plurality of frames.

In this case, as illustrated in a flowchart of FIG. 8, first, the image generation unit 31 generates an ultrasound image for each frame of the ultrasound images, and the ultrasound image is stored in the image memory 32 (step S31).

Subsequently, the excrement information detection unit 41 performs detection processing of an excrement region for each frame of the ultrasound images (step S32).

Subsequently, the movement amount detection unit 44 obtains a movement amount of the ultrasound image of the current frame for each frame of the ultrasound images (step S33). The movement amount detection unit 44 stores the movement amount obtained for each frame of the ultrasound images in the movement amount memory 38, as the movement amount of the ultrasound probe 1 (step S34).

As a result of detection processing of an excrement region, in a case where an excrement region is not detected from the ultrasound image of the current frame (No in step S35), the process returns to step S31, and detection processing of an excrement region is repeatedly performed until an excrement region is detected from the ultrasound image.

On the other hand, in a case where an excrement region is detected from the ultrasound image of the current frame (Yes in step S35), the movement amount detection unit 44 reads out, from the movement amount memory 38, the movement amounts of the ultrasound images of a predetermined number of previous frames (step S36), and obtains a statistic value from a movement amount group consisting of the movement amount of the ultrasound image of the current frame and the movement amounts of the ultrasound images of the predetermined number of previous frames that are read out from the movement amount memory 38 (step S37).

Subsequently, the highlight level determination unit 42 determines a highlight level based on the statistic value obtained from the movement amount group (step S38).

In addition, under the control of the display control unit 33, the excrement information display unit 43 highlight-displays the excrement region in the ultrasound image displayed on the monitor 34 according to the highlight level determined (changed) based on the statistic value obtained from the movement amount group (step S39).

Thereafter, the process returns to step S31, and the operation described above is repeated.

Alternatively, in a case where a statistic value is obtained from a group of the movement amounts of the ultrasound images of the plurality of frames, when an excrement region is detected, a group of the movement amounts of the ultrasound images of the plurality of frames may be obtained, and a statistic value may be obtained from the group of the movement amounts.

In this case, as illustrated in a flowchart of FIG. 9, operations of step S41 and step S42 are the same as the operations of step S31 and step S32 in the flowchart of FIG. 8.

As a result of detection processing of an excrement region, in a case where an excrement region is not detected from the ultrasound image of the current frame (No in step S43), the process returns to step S41, and detection processing of an excrement region is repeatedly performed until an excrement region is detected from the ultrasound image.

On the other hand, in a case where an excrement region is detected from the ultrasound image of the current frame (Yes in step S43), the movement amount detection unit 44 obtains a group of the movement amounts of the ultrasound images of the plurality of frames.

In this case, depending on a position of the frame of the previous ultrasound image in which the excrement region is detected, the frame of the previous ultrasound image being previous to the frame of the current ultrasound image in which the excrement region is detected by one frame, there are a case where all the movement amounts of the ultrasound images of a predetermined number of previous frames are not stored in the movement amount memory 38, a case where only some of the movement amounts of the ultrasound images of the previous frames are stored in the movement amount memory 38, and a case where all of the movement amounts of the ultrasound images of the previous frames are stored in the movement amount memory 38.

Therefore, in a case where the movement amount of the ultrasound image of the previous frame that is stored in the movement amount memory 38 is included in the movement amounts of the ultrasound images of the predetermined number of previous frames, the movement amount detection unit 44 reads out, from the movement amount memory 38, the movement amount of the ultrasound image of the previous frame that is stored in the movement amount memory 38, as a first movement amount (step S44).

In addition, in a case where the movement amount of the ultrasound image of the previous frame that is not stored in the movement amount memory 38 is included in the movement amounts of the ultrasound images of the predetermined number of previous frames, the movement amount detection unit 44 obtains the movement amount of the ultrasound image of the previous frame that is not stored in the movement amount memory 38, as a second movement amount (step S45), and further obtains the movement amount of the ultrasound image of the current frame, as a third movement amount (step S46). The movement amount detection unit 44 stores the second movement amount and the third movement amount in the movement amount memory 38, as the movement amount of the ultrasound probe 1 (step S47). In addition, the movement amount detection unit 44 obtains a statistic value from a movement amount group consisting of the first movement amount, the second movement amount, and the third movement amount (step S48).

Operations of step S49 and step S50 are the same as the operations of step S38 and step S39 in the flowchart of FIG. 8.

Thereafter, the process returns to step S41, and the operation described above is repeated.

The movement amount detection unit 44 may perform two-value determination for determining the movement of the ultrasound probe 1 with two-values indicating presence of movement or absence of movement, based on the movement amount of the ultrasound probe 1. In this case, the movement amount detection unit 44 detects whether or not there is movement of the ultrasound probe 1 by comparing the movement amount of the ultrasound probe 1 with a threshold value. That is, the movement amount detection unit 44 determines presence of movement in a case where the movement amount of the ultrasound probe 1 is equal to or larger than a threshold value, and determines absence of movement in a case where the movement amount of the ultrasound probe 1 is smaller than the threshold value.

In a case where the movement amount detection unit 44 performs two-value determination of the movement of the ultrasound probe 1, for example, the highlight level determination unit 42 determines a first highlight level in a case where presence of movement is determined, and determines a second highlight level lower than the first highlight level in a case where absence of movement is determined, the first highlight level and the second highlight level being two-stage highlight levels corresponding to the movement of the ultrasound probe 1 with two-values, that is, highlight levels corresponding to presence of movement and absence of movement.

Further, in a case where a determination result of the two-value determination is changed, for example, the highlight level determination unit 42 changes the highlight level in the ultrasound image of the frame immediately after the determination result of the two-value determination is changed, to the highlight level of the stage corresponding to the changed determination result of the two-value determination.

Further, the movement amount detection unit 44 may perform multi-value determination for determining the movement of the ultrasound probe 1 with multi-values of three or more values based on the movement amount of the ultrasound probe 1. In this case, the movement amount detection unit 44 detects the movement of the ultrasound probe 1 with multi-values by comparing the movement amount of the ultrasound probe 1 with each of threshold values having multi-values. For example, the movement amount detection unit 44 detects the movement of the ultrasound probe 1 with (n+1) values by comparing the movement amount of the ultrasound probe 1 with each of n threshold values that are continuously converted.

In a case where the movement amount detection unit 44 performs multi-value determination of the movement of the ultrasound probe 1, for example, the highlight level determination unit 42 determines, as the highlight level, a highlight level of a stage corresponding to a determination result of the multi-value determination, from among multi-stage highlight levels corresponding to the movement of the ultrasound probe 1 with multi-values.

Further, in a case where the determination result of the multi-value determination is changed, for example, the highlight level determination unit 42 changes the highlight level in the ultrasound image of the frame immediately after the determination result of the multi-value determination is changed, to the highlight level of the stage corresponding to the changed determination result of the multi-value determination. Alternatively, in a case where the determination result of the multi-value determination is changed by two or more values, the highlight level determination unit 42 may gradually change the highlight level in the ultrasound images of the plurality of frames after the determination result of the multi-value determination is changed, from the highlight level of the stage corresponding to the determination result of the multi-value determination before the change to the highlight level of the stage corresponding to the determination result of the multi-value determination after the change.

Next, a method of highlight-displaying the excrement region will be described with reference to a specific example.

The excrement information display unit 43 can create, for example, a mask obtained by coloring and filling the inside of the excrement region with a predetermined display color, change transparency of the display color according to the highlight level of the excrement region that is determined by the highlight level determination unit 42, and display the mask of which the transparency is changed by superimposing the mask on the excrement region of the ultrasound image displayed on the monitor 34.

Figure 10A:
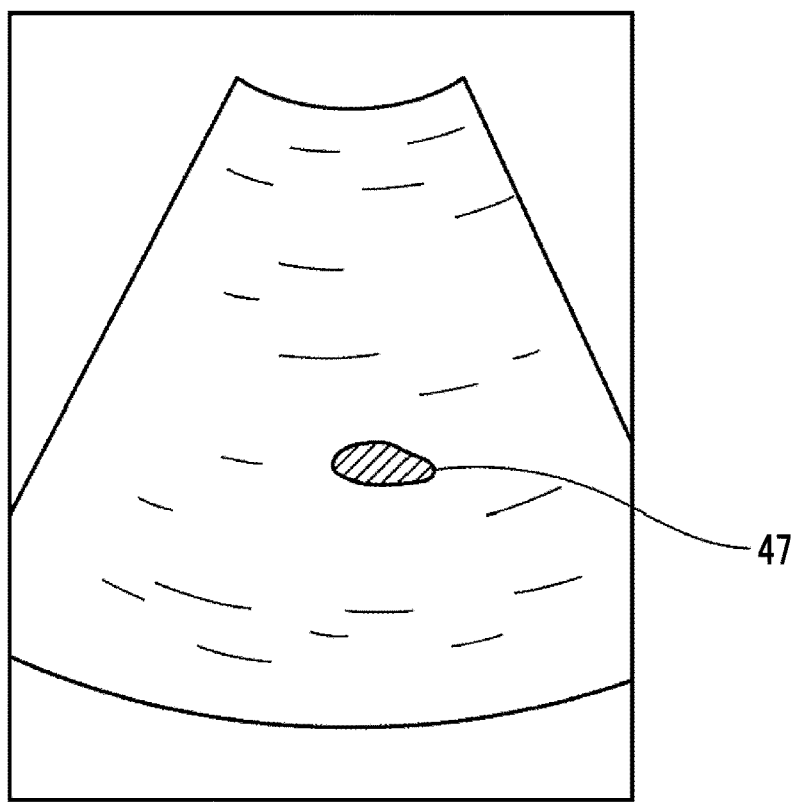
FIG. 10A is a conceptual diagram of an embodiment illustrating a display screen of a monitor of the ultrasound diagnostic apparatus in a case where transparency of a mask is decreased according to a highlight level.
Figure 10B:
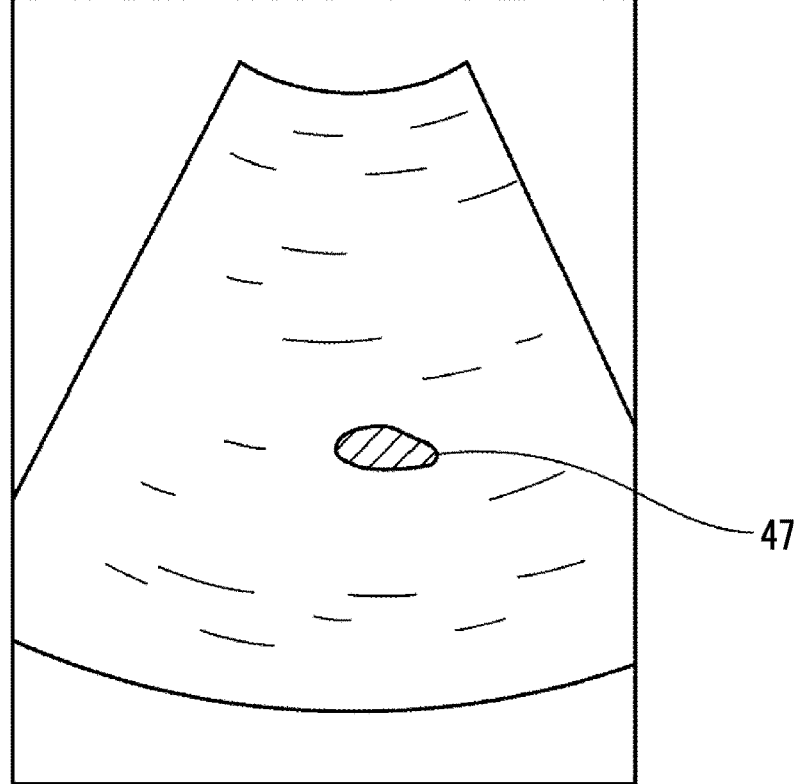
FIG. 10B is a conceptual diagram of an embodiment illustrating a display screen of a monitor of the ultrasound diagnostic apparatus in a case where transparency of a mask is increased according to a highlight level.

In this case, the excrement information display unit 43 displays the mask 47 by decreasing the transparency of the mask 47 as the highlight level is higher, as illustrated in FIG. 10A, and increasing the transparency of the mask 47 as the highlight level is lower, as illustrated in FIG. 10B. In FIG. 10A and FIG. 10B, a difference in the transparency is represented by a coarseness and fineness of hatching. That is, hatching in a case where the transparency is lower as illustrated in FIG. 10A is dense, and hatching in a case where the transparency is higher as illustrated in FIG. 10B is coarse.

Alternatively, the excrement information display unit 43 can create a contour line by detecting a contour of the excrement region, change a thickness of the contour line or transparency of a display color of the contour line according to the highlight level of the excrement region, and display the contour line of which the thickness or the transparency is changed by superimposing the contour line on the contour of the excrement region of the ultrasound image displayed on the monitor 34.

Figure 11A:
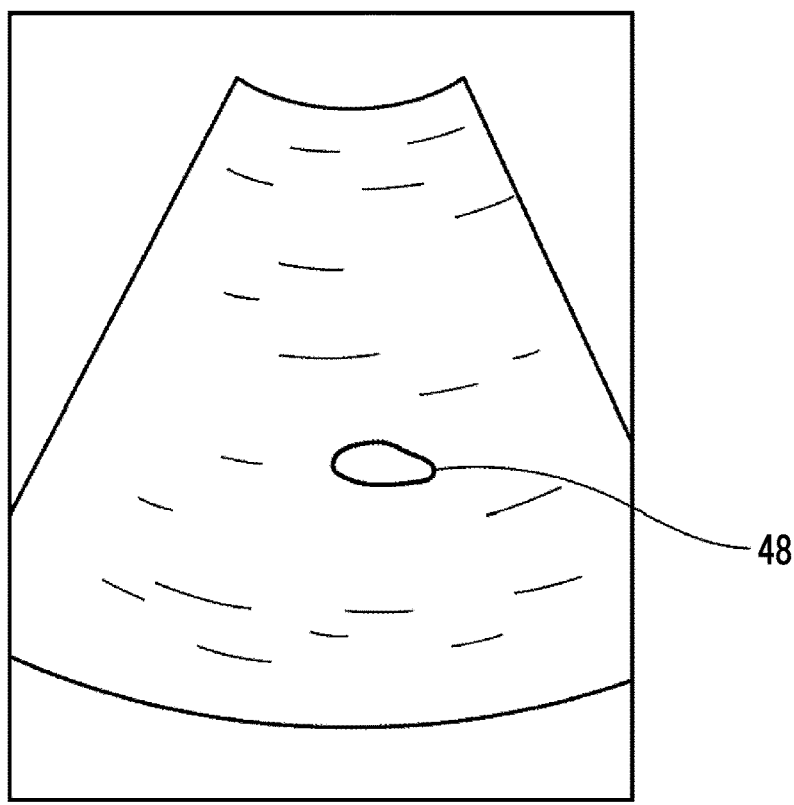
FIG. 11A is a conceptual diagram of an embodiment illustrating a display screen of a monitor of the ultrasound diagnostic apparatus in a case where a thickness of a contour line is increased according to a highlight level.
Figure 11B:
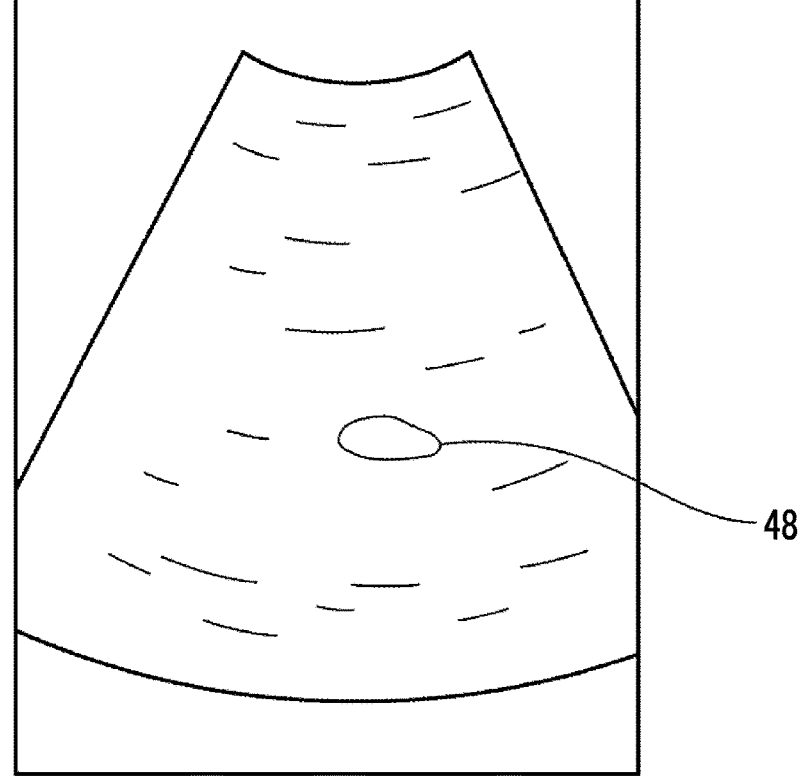
FIG. 11B is a conceptual diagram of an embodiment illustrating a display screen of a monitor of the ultrasound diagnostic apparatus in a case where a thickness of a contour line is decreased according to a highlight level.

In this case, the excrement information display unit 43 displays the contour line by increasing the thickness of the contour line 48 as the highlight level is higher as illustrated in FIG. 11A, and decreasing the thickness of the contour line 48 as the highlight level is lower as illustrated in FIG. 11B. In addition, as in the case of the mask 47, the excrement information display unit 43 displays the contour line 48 by increasing the transparency of the contour line 48 as the highlight level is lower, and decreasing the transparency of the contour line 48 as the highlight level is higher.

Figure 12A:
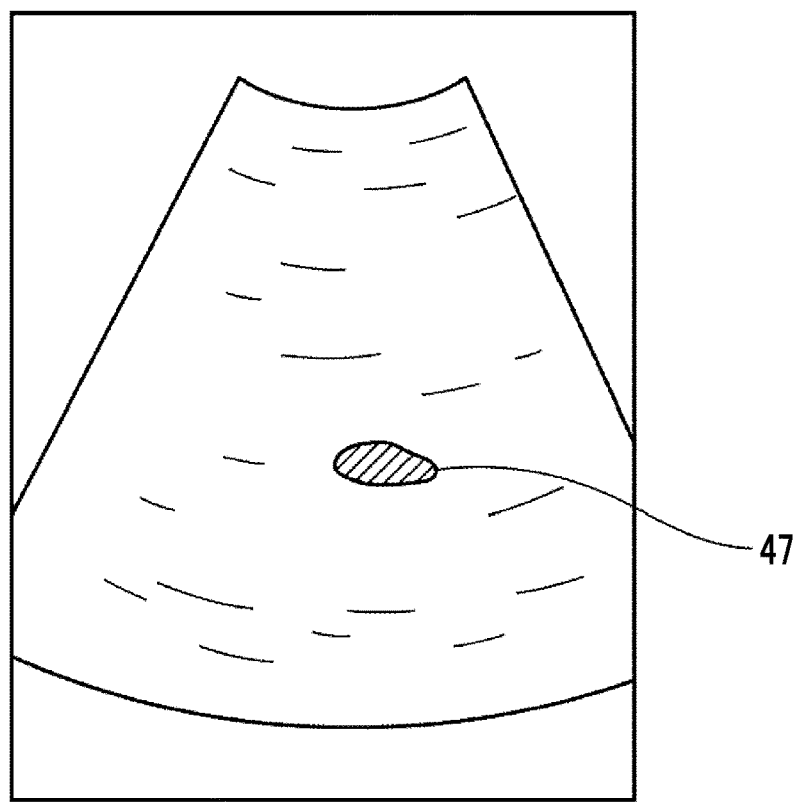
FIG. 12A is a conceptual diagram of an embodiment illustrating a display screen of a monitor of the ultrasound diagnostic apparatus in a case where a display form of highlight-display is set as a mask according to a highlight level.
Figure 12B:
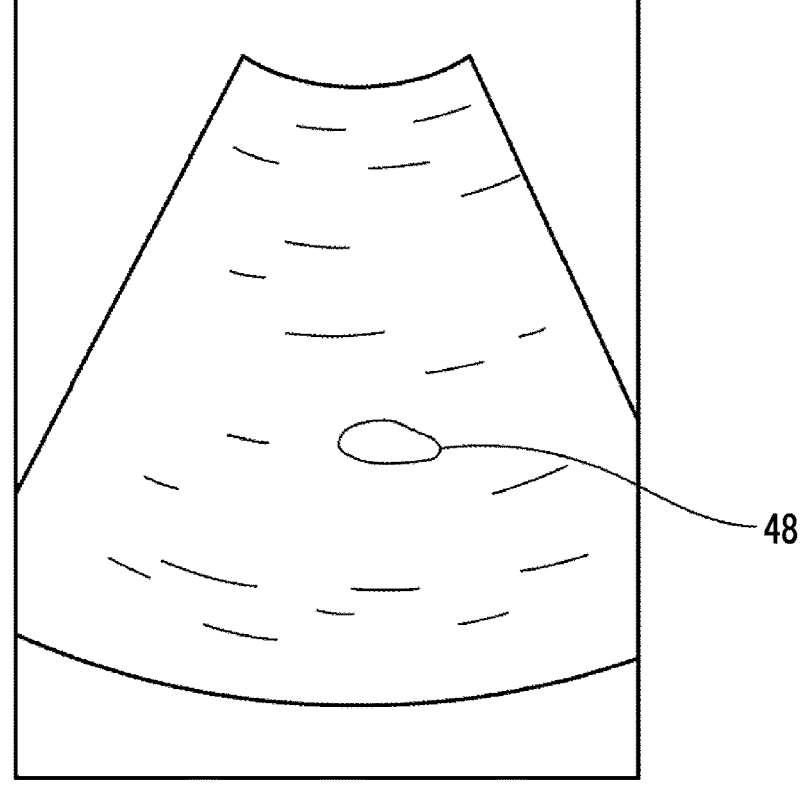
FIG. 12B is a conceptual diagram of an embodiment illustrating a display screen of a monitor of the ultrasound diagnostic apparatus in a case where a display form of highlight-display is set as a contour line according to a highlight level.

Further, the excrement information display unit 43 may change a display form of the highlight display from a mask to a contour line, or may change a display form of the highlight-display from a contour line to a mask, according to the highlight level of the excrement region. In this case, for example, in a case where the highlight level of the excrement region is equal to or higher than the threshold value, that is, in a case where the highlight level of the excrement region is increased, the excrement information display unit 43 creates the above-described mask 47, and displays the mask 47 by superimposing the mask 47 on the excrement region as illustrated in FIG. 12A. On the other hand, in a case where the highlight level of the excrement region is lower than the threshold value, that is, in a case where the highlight level of the excrement region is decreased, the excrement information display unit 43 creates the above-described contour line 48, and displays the contour line 48 by superimposing the contour line 48 on the contour of the excrement region as illustrated in FIG. 12B.

The excrement information display unit 43 may highlight-display the excrement region by thinning out a frame for highlight-display according to the highlight level of the excrement region that is determined by the highlight level determination unit 42. In this case, the user can see that the highlight-display of the excrement region is blinking. Accordingly, a ratio between the number of frames (time) in which the excrement region is highlight-displayed and the number of frames (time) in which the excrement region is not highlight-displayed, that is, a degree of blinking of the highlight-display of the excrement region can be changed according to the highlight level of the excrement region.

For example, the excrement information display unit 43 increases a time for which the excrement region is highlight-displayed by decreasing the number of frames to be thinned out, as the highlight level of the excrement region is higher, and decreases a time for which the excrement region is highlight-displayed by increasing the number of frames to be thinned out, as the highlight level of the excrement region is lower. For example, in a case where the highlight level is increased, the excrement information display unit 43 may thin out the frames such that a blinking interval is shortened, or may thin out the frames such that a time for which the excrement region is highlight-displayed is lengthened.

In a case where the excrement information detection unit 41 performs detection processing for detecting an excrement property of the excrement region from the ultrasound image, in addition to the detection of the excrement region, the excrement information display unit 43 may change the display color of the highlight-display of the excrement region according to, for example, the excrement property such as hard excrement, soft excrement, or normal excrement in a case where the excrement property of the excrement region is detected from the ultrasound image as a result of detection processing of the excrement property. Thereby, the user can recognize the excrement property only by looking at the display color of the highlight-display of the excrement region.

The excrement property of the excrement region is not changed during scanning. On the other hand, the excrement information detection unit 41 may erroneously detect the excrement property of the excrement region depending on a state where the ultrasound probe 1 is brought into contact with the examination area of the subject. However, in a state where the highlight level of the display color of the highlight-display of the excrement region, for example, the transparency is decreased, in a case where the excrement property of the excrement region is changed and thus the display color of the highlight-display of the excrement region is changed, it is difficult for the user to recognize the change of the display color of the highlight-display of the excrement region.

Therefore, the highlight level determination unit 42 performs the above-described identity determination of the excrement region. In a case where a detection result of the excrement property of the excrement region determined to be the same is changed, that is, in a case where the excrement property of the excrement region is erroneously determined, the highlight level of the excrement region may be temporarily increased.

The excrement information display unit 43 highlight-displays the excrement region according to the temporarily-increased highlight level of the excrement region.

In addition, after a lapse of a predetermined period from a change of the detection result of the excrement property, the highlight level determination unit 42 returns the highlight level to the highlight level of the excrement region before increasing the highlight level, and then determines a highlight level of the excrement region based on the determination condition of the highlight level.

As described above, in a case where the excrement property of the excrement region is changed, by temporarily increasing the highlight level of the excrement region, the user can be alerted to a possibility that the excrement property may be erroneously detected.

Figure 13:
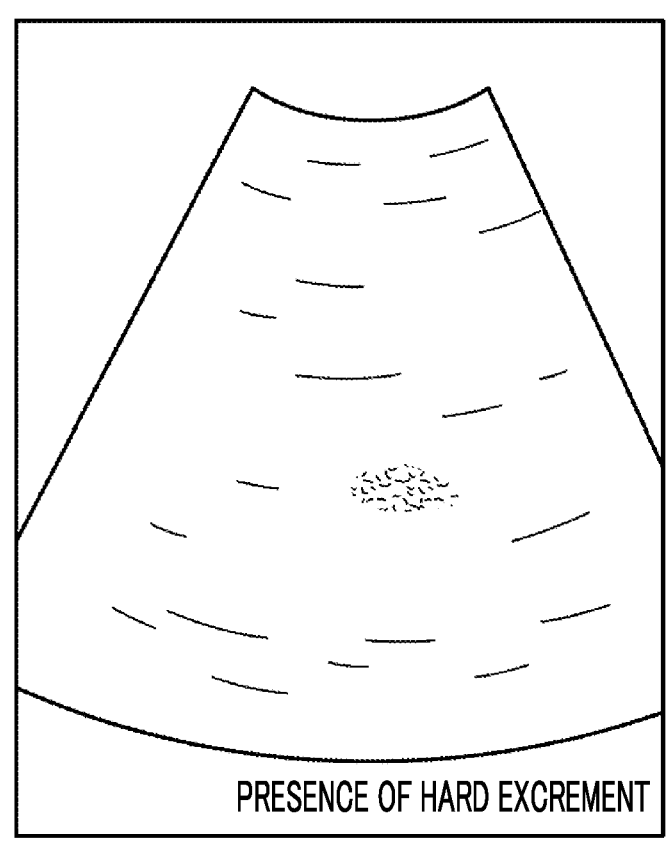
FIG. 13 is a conceptual diagram of an embodiment illustrating a display screen of a monitor of the ultrasound diagnostic apparatus in a case where a detection result of an excrement property is displayed as text information.

As illustrated in FIG. 13, the excrement information display unit 43 may display, as text information, the detection result of the excrement property such as "hard excrement" on the monitor 34. In this case, the excrement region may be highlight-displayed, and the text information may be displayed. Alternatively, the excrement region may not be highlight-displayed and only the text information may be displayed. Thereby, even in a case where the excrement region is not highlight-displayed, or even in a case where the highlight level of the highlight-display of the excrement region is lower, the user can recognize the excrement property only by looking at the text information.

The present invention is not limited to a stationary ultrasound diagnostic apparatus, and can be similarly applied to a portable ultrasound diagnostic apparatus in which an apparatus main body 3 is realized by a laptop terminal device, and a handheld ultrasound diagnostic apparatus in which an apparatus main body 3 is realized by a handheld terminal device such as a smartphone or a tablet personal computer (PC). In addition, the ultrasound probe 1 and the apparatus main body 3 may be connected in a wired or wireless manner. Further, the entire image generation unit 31 or only the signal processing unit 16 may be provided on the ultrasound probe 1 side, or provided on the apparatus main body 3 side.

In the apparatus of the present invention, as the hardware configurations of the processing units that execute various kinds of processing, such as the transmission/reception circuit 14, the image generation unit 31, the display control unit 33, the excrement processing unit 35, and the apparatus control unit 36, dedicated hardware may be used, or various processors or computers that execute programs may be used.

Further, as the image memory 32 and the movement amount memory 38, recording media such as a flash memory, a hard disk drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), and a universal serial bus memory (USB memory), an external server, or the like can be used.

The various processors include a central processing unit (CPU), which is a general-purpose processor that executes software (program) and functions as the various processing units, a programmable logic device (PLD), which is a processor of which a circuit configuration can be changed after manufacture, such as a field programmable gate array (FPGA), and a dedicated electric circuit, which is a processor having a circuit configuration that is designed for exclusive use in order to execute specific processing, such as an application specific integrated circuit (ASIC).

One processing unit may be configured by using one of the various processors or may be configured by using a combination of two or more processors of the same type or different types, for example, a combination of a plurality of FPGAs or a combination of an FPGA and a CPU. In addition, a plurality of processing units may be configured by using one of various processors, or two or more of the plurality of processing units may be collectively configured by using one processor.

For example, first, as represented by a computer, such as a client and a server, there is a form in which one processor is configured by using a combination of one or more CPUs and software and this processor functions as the plurality of processing units. In addition, as represented by a system on chip (SoC) or the like, there is a form in which a processor that realizes functions of an entire system including a plurality of processing units with one integrated circuit (IC) chip is used.

Further, the hardware configuration of these various processors is, more specifically, an electric circuit (circuitry) in which circuit elements, such as semiconductor elements, are combined.

In addition, the method according to the embodiment of the present invention can be implemented, for example, by a program for causing a computer to execute each of the steps of the method. In addition, a computer-readable recording medium on which the program is recorded can be provided.

Although the present invention is described in detail above, the present invention is not limited to the embodiment described above, and it is needless to say that various improvements or changes may be made without departing from the gist of the present invention.

EXPLANATION OF REFERENCES

1: ultrasound probe
3: apparatus main body
11: transducer array
12: motion sensor
14: transmission/reception circuit
16: signal processing unit
17: image processing unit
18: DSC
31: image generation unit
32: image memory
33: display control unit
34: monitor
35: excrement processing unit
36: apparatus control unit
37: input device
38: movement amount memory
39: processor
41: excrement information detection unit
42: highlight level determination unit
43: excrement information display unit
44: movement amount detection unit
46: mode switching unit
47: mask
48: contour line
51: pulser
52: amplification unit
53: AD conversion unit
54: beam former

What is claimed is:

1. An ultrasound diagnostic apparatus comprising:
an ultrasound probe;
a monitor; and
a processor; wherein the processor is configured to:
generate an ultrasound image based on a reception signal obtained by scanning an examination area of a subject with ultrasound beams using the ultrasound probe;
display the ultrasound image on the monitor;
perform detection processing for detecting an excrement region from the ultrasound image;
determine a highlight level of the excrement region based on a determination condition for determining the highlight level of the excrement region in a case where the excrement region is detected; and
highlight-display the excrement region in the ultrasound image displayed on the monitor according to the determined highlight level,
wherein the processor detects the excrement region from the ultrasound image by using at least one of template matching between the ultrasound image and each of a plurality of templates differing in at least one of size, shape, and texture of an excrement region, machine learning using image feature amounts of a plurality of first ultrasound images including anatomical structures and excrement regions, or a deep learning model obtained by learning, for a plurality of second ultrasound images, a relationship between a second ultrasound image and an excrement region included in the second ultrasound image,
wherein the determination condition is at least one of a movement amount of the ultrasound probe, a continuous display time of an identical excrement region included in ultrasound images of a plurality of frames, an area of the excrement region, or an instruction from a user,
wherein the highlight level of the excrement region controls at least one of transparency of a display color of a mask obtained by coloring and filling an inside of the excrement region, thickness of a contour line of the excrement region or transparency of a display color of the contour line, or a thinning-out rate of frames of ultrasound images for highlight-displaying the excrement region, and
wherein the thinning-out rate indicates a ratio between a number of frames in which the excrement region is highlight-displayed and a number of frames in which the excrement region is not highlight-displayed.

2. The ultrasound diagnostic apparatus according to claim 1,
wherein the determination condition is the movement amount of the ultrasound probe,
wherein the processor is configured to detect the movement amount of the ultrasound probe, and
wherein the processor determines the highlight level based on the movement amount in the case where the excrement region is detected.

3. The ultrasound diagnostic apparatus according to claim 2,
wherein the processor obtains, for each frame of the ultrasound images, a correlation value between an ultrasound image of a current frame and an ultrasound image of a previous frame that is previous to the current frame by one frame, as the movement amount.

4. The ultrasound diagnostic apparatus according to claim 2,
wherein the processor obtains, for each frame of the ultrasound images, a correlation value between an ultrasound image of a current frame and an ultrasound image of a previous frame that is previous to the ultrasound image of the current frame by a predetermined number of frames, as the movement amount.

5. The ultrasound diagnostic apparatus according to claim 2,
wherein the processor obtains, for each frame of the ultrasound images, a degree of superimposition between the excrement region of an ultrasound image of a current frame and the excrement region of an ultrasound image of a previous frame that is previous to the current frame by one frame, as the movement amount.

6. The ultrasound diagnostic apparatus according to claim 2,
wherein the processor obtains, for each frame of the ultrasound images, a movement amount between an ultrasound image of a current frame and an ultrasound image of a previous frame that is previous to the current frame by one frame, as a movement amount of the ultrasound image of the current frame, and obtains a statistic value obtained from a movement amount group consisting of the movement amount of the ultrasound image of the current frame and movement amounts of ultrasound images of a predetermined number of previous frames, as the movement amount.

7. The ultrasound diagnostic apparatus according to claim 6, wherein the statistic value is an average value obtained from the movement amount group, a weighted average value obtained from the movement amount group by using a weight increasing from a past to a present, or a median value obtained from the movement amount group.

8. The ultrasound diagnostic apparatus according to claim 6, further comprising:

a movement amount memory that stores the movement amount, wherein the processor performs the detection processing of the excrement region for each frame of the ultrasound images, and the processor obtains the movement amount for each frame of the ultrasound images, and stores the movement amount in the movement amount memory, and in a case where the excrement region is detected, reads out the movement amounts of the ultrasound images of the predetermined number of previous frames from the movement amount memory, and obtains the statistic value from the movement amount group consisting of the movement amount of the ultrasound image of the current frame and the movement amounts of the ultrasound images of the previous frames that are read out from the movement amount memory.

9. The ultrasound diagnostic apparatus according to claim 6, further comprising:

a movement amount memory that stores the movement amount, wherein the processor performs the detection processing of the excrement region for each frame of the ultrasound images, and in a case where the excrement region is detected, the processor reads out, from the movement amount memory, the movement amount of the ultrasound image of the previous frame that is stored in the movement amount memory, as a first movement amount, in a case where the movement amount of the ultrasound image of the previous frame that is stored in the movement amount memory is included in the movement amounts of the ultrasound images of the predetermined number of previous frames, obtains the movement amount of the ultrasound image of the previous frame that is not stored in the movement amount memory, as a second movement amount, in a case where the movement amount of the ultrasound image of the previous frame that is not stored in the movement amount memory is included in the movement amounts of the ultrasound images of the predetermined number of previous frames, obtains the movement amount of the ultrasound image of the current frame, as a third movement amount, stores the second movement amount and the third movement amount in the movement amount memory, and obtains the statistic value from a movement amount group consisting of the first movement amount, the second movement amount, and the third movement amount.

10. The ultrasound diagnostic apparatus according to claim 2, wherein the processor detects the movement amount based on a movement detection result by a motion sensor provided in the ultrasound probe.

11. The ultrasound diagnostic apparatus according to claim 3, wherein the processor performs two-value determination for determining movement of the ultrasound probe with two-values indicating presence of movement or absence of movement, based on the movement amount, and the processor determines a first highlight level in a case where presence of the movement is determined, and determines a second highlight level lower than the first highlight level in a case where absence of the movement is determined, the first highlight level and the second highlight level being two-stage highlight levels corresponding to the movement of the ultrasound probe with two-values.

12. The ultrasound diagnostic apparatus according to claim 3, wherein the processor performs multi-value determination for detecting movement of the ultrasound probe with multi-values of three or more values, based on the movement amount, and the processor determines, as the highlight level, a highlight level of a stage corresponding to a determination result of the multi-value determination, from among multi-stage highlight levels corresponding to the movement of the ultrasound probe with multi-values.

13. The ultrasound diagnostic apparatus according to claim 12, wherein in a case where the determination result of the multi-value determination is changed, the processor changes the highlight level in an ultrasound image of a frame immediately after the determination result of the multi-value determination is changed, to a highlight level of a stage corresponding to the determination result of the multi-value determination after the change.

14. The ultrasound diagnostic apparatus according to claim 12, wherein in a case where the determination result of the multi-value determination is changed by two or more values, the processor gradually changes the highlight level in ultrasound images of a plurality of frames after the determination result of the multi-value determination is changed, from a highlight level of a stage corresponding to the determination result of the multi-value determination before the change to a highlight level of a stage corresponding to the determination result of the multi-value determination after the change.

15. The ultrasound diagnostic apparatus according to claim 1, wherein in a case of detecting excrement regions from ultrasound images of a plurality of frames, the processor performs identity determination to determine whether or not the excrement regions in ultrasound images of adjacent frames are the identical excrement region, and determines the highlight level based on the continuous display time of the excrement region determined to be the same.

16. The ultrasound diagnostic apparatus according to claim 1, wherein the processor determines the highlight level based on the area of the excrement region.

17. The ultrasound diagnostic apparatus according to claim 1, wherein the processor creates the mask obtained by coloring and filling the inside of the excrement region with a predetermined display color, changes the transparency of the display color according to the highlight level, and displays the mask of which the transparency is changed by superimposing the mask on the excrement region.

18. The ultrasound diagnostic apparatus according to claim 1,
wherein the processor creates a contour line by detecting a contour of the excrement region, changes a thickness of the contour line or transparency of a display color of the contour line according to the highlight level, and displays the contour line of which the thickness or the transparency is changed by superimposing the contour line on the contour of the excrement region.

19. The ultrasound diagnostic apparatus according to claim 1,
wherein in a case where the highlight level is equal to or higher than a threshold value, the processor creates the mask obtained by coloring and filling the inside of the excrement region with a predetermined display color, and displays the mask by superimposing the mask on the excrement region, and
in a case where the highlight level is lower than the threshold value, the processor creates the contour line by detecting a contour of the excrement region, and displays the contour line by superimposing the contour line on the contour of the excrement region.

20. The ultrasound diagnostic apparatus according to claim 1,
wherein the processor highlight-displays the excrement region by thinning out a frame for the highlight-display according to the highlight level.

21. The ultrasound diagnostic apparatus according to claim 1,
wherein the processor further performs detection processing for detecting an excrement property of the excrement region from the ultrasound image, and
the processor changes a display color of the highlight-display of the excrement region according to the excrement property in a case where the excrement property is detected.

22. The ultrasound diagnostic apparatus according to claim 21,
wherein the processor detects a statistic value of brightness in the excrement region for each frame of the ultrasound images, obtains a first comparison result by comparing the statistic value of brightness in the excrement region with a threshold value, and detects the excrement property based on the first comparison result in ultrasound images of one frame or a plurality of frames, or
the processor detects a brightness ratio between the statistic value of the brightness in the excrement region and a statistic value of brightness in a predetermined region around the excrement region for each frame of the ultrasound images, obtains a second comparison result by comparing the brightness ratio with a threshold value, and detects the excrement property based on the second comparison result in ultrasound images of one frame or a plurality of frames.

23. The ultrasound diagnostic apparatus according to claim 21,
wherein the processor detects the excrement region by using a deep learning model.

24. The ultrasound diagnostic apparatus according to claim 21,
wherein the processor
performs identity determination to determine whether or not the excrement regions of ultrasound images of adjacent frames are the identical excrement region, and
temporarily increases the highlight level in a case where a detection result of the excrement property of the excrement region determined to be the same is changed.

25. The ultrasound diagnostic apparatus according to claim 21,
wherein the processor displays a detection result of the excrement property on the monitor as text information.

26. The ultrasound diagnostic apparatus according to claim 1,
wherein the processor changes the highlight level according to the instruction from the user.

27. The ultrasound diagnostic apparatus according to claim 1,
wherein the ultrasound diagnostic apparatus has at least two operation modes among a first operation mode in which the excrement region is not highlight-displayed, a second operation mode in which the excrement region is highlight-displayed at a predetermined highlight level regardless of the determination condition, and a third operation mode in which the highlight level is determined based on the determination condition and the excrement region is highlight-displayed, and
wherein the processor is configured to switch an operation mode to one operation mode among the at least two operation modes according to the instruction from the user.

28. A control method for an ultrasound diagnostic apparatus, the method comprising:
generating, via a processor, an ultrasound image based on a reception signal obtained by scanning an examination area of a subject with ultrasound beams using an ultrasound probe;
displaying, via the processor, the ultrasound image on a monitor;
performing, via the processor, detection processing for detecting an excrement region from the ultrasound image;
determining, via the processor, a highlight level of the excrement region based on a determination condition for determining the highlight level of the excrement region in a case where the excrement region is detected; and
highlight-displaying, via the processor, the excrement region in the ultrasound image displayed on the monitor according to the determined highlight level,
wherein the processor detects the excrement region from the ultrasound image by using at least one of template matching between the ultrasound image and each of a plurality of templates differing in at least one of size, shape, and texture of an excrement region, machine learning using image feature amounts of a plurality of first ultrasound images including anatomical structures and excrement regions, or a deep learning model obtained by learning, for a plurality of second ultrasound images, a relationship between a second ultrasound image and an excrement region included in the second ultrasound image,
wherein the determination condition is at least one of a movement amount of the ultrasound probe, a continuous display time of an identical excrement region included in ultrasound images of a plurality of frames, an area of the excrement region, or an instruction from a user, wherein the highlight level of the excrement region controls at least one of transparency of a display color of a mask obtained by coloring and filling an inside of the excrement region, thickness of a contour line of the excrement region or transparency of a display color of the contour line, or a thinning-out rate of frames of ultrasound images for highlight-displaying the excrement region, and wherein the thinning-out rate indicates a ratio between a number of frames in which the excrement region is highlight-displayed and a number of frames in which the excrement region is not highlight-displayed.

* * * * *